United States Patent
DeVries et al.

(10) Patent No.: US 10,596,903 B2
(45) Date of Patent: Mar. 24, 2020

(54) NETWORKED INTOXICATION VEHICLE IMMOBILIZATION

(71) Applicant: Consumer Safety Technology, LLC, Des Moines, IA (US)

(72) Inventors: Douglas Edward DeVries, Johnston, IA (US); Timothy J. McGrath, Saint Petersburg, FL (US)

(73) Assignee: Consumer Safety Technology, LLC, Des Moines, IA (US)

( * ) Notice: Subject to any disclaimer, the term of this patent is extended or adjusted under 35 U.S.C. 154(b) by 0 days.

(21) Appl. No.: 16/543,274

(22) Filed: Aug. 16, 2019

(65) Prior Publication Data

US 2019/0366845 A1 Dec. 5, 2019

Related U.S. Application Data

(63) Continuation of application No. 15/223,921, filed on Jul. 29, 2016.

(Continued)

(51) Int. Cl.
*B60K 28/06* (2006.01)
*B60R 25/00* (2013.01)
(Continued)

(52) U.S. Cl.
CPC ............ *B60K 28/063* (2013.01); *A61B 5/082* (2013.01); *B60K 28/066* (2013.01); *B60R 25/00* (2013.01);
(Continued)

(58) Field of Classification Search
CPC ................ B60K 25/063; B60K 28/066; B60K 2370/589; G07C 5/008; H04W 4/80;
(Continued)

(56) References Cited

U.S. PATENT DOCUMENTS 3,824,167 A 7/1974 Oswin et al.
3,847,551 A 11/1974 Hutson et al.
(Continued)

FOREIGN PATENT DOCUMENTS

AU 2001097152 6/2002
AU 2011256122 12/2013
(Continued)

OTHER PUBLICATIONS

"File History," for U.S. Appl. No. 15/223,894 downloaded Sep. 24, 2019 (404 pages).
(Continued)

*Primary Examiner* — Karen Beck
(74) *Attorney, Agent, or Firm* — Pauly, DeVries Smith & Deffner LLC

(57) ABSTRACT

A vehicle immobilization system includes a detection element operable to detect a level of an intoxicant in a user's breath. A control module is operable to receive a signal from the detection element indicating the level of intoxicant in the user's breath, and to selectively restrict operation of a vehicle based on the level of intoxicant in the user's breath exceeding a threshold. A wireless relay is operable to replace a standard relay in the vehicle, and to wirelessly communicate with the control module such that the control module is operable to control the wireless relay to selectively restrict operation of the vehicle.

20 Claims, 7 Drawing Sheets

Related U.S. Application Data

(60) Provisional application No. 62/240,978, filed on Oct. 13, 2015, provisional application No. 62/266,279, filed on Dec. 11, 2015, provisional application No. 62/306,177, filed on Mar. 10, 2016.

(51) Int. Cl.

| | | |
|---|---|---|
| *B60R 25/045* | (2013.01) | |
| *H04W 4/80* | (2018.01) | |
| *A61B 5/08* | (2006.01) | |
| *G07C 5/00* | (2006.01) | |
| *H04B 7/26* | (2006.01) | |
| *A61B 10/00* | (2006.01) | |

(52) U.S. Cl.
CPC ............ *B60R 25/045* (2013.01); *G07C 5/008* (2013.01); *H04W 4/80* (2018.02); *A61B 2010/0009* (2013.01); *A61B 2010/0087* (2013.01); *B60K 2370/589* (2019.05); *B60R 2325/101* (2013.01); *B60W 2540/24* (2013.01); *B60Y 2400/30* (2013.01); *H04B 7/26* (2013.01)

(58) Field of Classification Search
CPC ............ A61B 5/082; A61B 2010/0009; A61B 2010/0087; B60R 25/045; B60R 25/00; B60R 2325/101; H04B 7/26; B60W 2540/24; B60Y 2400/30
See application file for complete search history.

(56) References Cited

U.S. PATENT DOCUMENTS

| | | | |
|---|---|---|---|
| 3,854,319 | A | 12/1974 | Burroughs et al. |
| 3,877,291 | A | 4/1975 | Hoppesch et al. |
| 3,948,604 | A | 4/1976 | Hoppesch et al. |
| 4,034,743 | A | 7/1977 | Greenwood et al. |
| 4,093,945 | A | 6/1978 | Collier et al. |
| 4,158,198 | A | 6/1979 | Ochiai et al. |
| 4,278,636 | A | 7/1981 | Boldt et al. |
| 4,407,152 | A | 10/1983 | Guth et al. |
| 4,448,058 | A | 5/1984 | Jaffe et al. |
| 4,481,804 | A | 11/1984 | Eberhard et al. |
| 4,487,055 | A | 12/1984 | Wolf et al. |
| 4,592,443 | A | 6/1986 | Simon |
| 4,656,008 | A | 4/1987 | Gump |
| 4,678,057 | A | 7/1987 | Elfman et al. |
| 4,680,956 | A | 7/1987 | Huszczuk |
| 4,697,666 | A | 10/1987 | Collier et al. |
| 4,722,217 | A | 2/1988 | Arnett et al. |
| 4,749,553 | A | 6/1988 | Phillips et al. |
| 4,809,810 | A | 3/1989 | Elfman et al. |
| 4,854,153 | A | 8/1989 | Miyagawa et al. |
| 4,901,058 | A | 2/1990 | Comeau et al. |
| 4,912,458 | A | 3/1990 | Comeau et al. |
| 4,914,038 | A | 4/1990 | Jewitt et al. |
| 4,956,561 | A | 9/1990 | Tamer |
| 4,970,172 | A | 11/1990 | Kundu |
| 5,058,601 | A | 10/1991 | Riker |
| 5,069,220 | A | 12/1991 | Casparie et al. |
| 5,134,875 | A | 8/1992 | Jensen et al. |
| 5,239,492 | A | 8/1993 | Hartwig et al. |
| 5,303,575 | A | 4/1994 | Brown et al. |
| 5,303,712 | A | 4/1994 | Van |
| 5,400,637 | A | 3/1995 | Forrester et al. |
| 5,422,485 | A | 6/1995 | Bowlds |
| 5,426,415 | A | 6/1995 | Prachar et al. |
| 5,443,794 | A | 8/1995 | Williams |
| 5,455,734 | A | 10/1995 | Foreman et al. |
| 5,493,891 | A | 2/1996 | Slemeyer |
| 5,568,348 | A | 10/1996 | Foreman et al. |
| 5,622,164 | A | 4/1997 | Kilis et al. |
| 5,665,894 | A | 9/1997 | Baker |
| 5,705,735 | A | 1/1998 | Acorn |
| 5,734,090 | A | 3/1998 | Koppel et al. |
| 5,866,794 | A | 2/1999 | Stock |
| 6,026,674 | A | 2/2000 | Gammenthaler et al. |
| 6,075,444 | A | 6/2000 | Sohege et al. |
| 6,079,251 | A | 6/2000 | Gaultier et al. |
| 6,096,558 | A | 8/2000 | Stock et al. |
| 6,167,746 | B1 | 1/2001 | Gammenthaler |
| 6,174,289 | B1 | 1/2001 | Binder |
| 6,206,130 | B1 | 3/2001 | Hetler et al. |
| 6,206,837 | B1 | 3/2001 | Brugnoli |
| 6,244,093 | B1 | 6/2001 | Parekh |
| 6,442,639 | B1 | 8/2002 | Mcelhattan et al. |
| 6,475,158 | B1 | 11/2002 | Orr et al. |
| 6,526,802 | B1 | 3/2003 | Fisher et al. |
| 6,611,201 | B1 | 8/2003 | Bishop et al. |
| 6,656,127 | B1 | 12/2003 | Ben-oren et al. |
| 6,664,888 | B1 | 12/2003 | Bishop et al. |
| 6,697,732 | B1 | 2/2004 | Gotfried et al. |
| 6,726,636 | B2 | 4/2004 | Der et al. |
| 6,748,792 | B1 | 6/2004 | Freund et al. |
| 6,784,567 | B1 | 8/2004 | Klitzner |
| 6,824,520 | B2 | 11/2004 | Orr et al. |
| 6,853,956 | B2 | 2/2005 | Ballard et al. |
| 6,918,281 | B2 | 7/2005 | Sussman et al. |
| 6,956,484 | B2 | 10/2005 | Crespo et al. |
| 6,967,581 | B2 | 11/2005 | Karsten |
| 6,980,124 | B2 | 12/2005 | Kong et al. |
| 7,061,137 | B2 | 6/2006 | Flick et al. |
| 7,103,454 | B2 | 9/2006 | Stock et al. |
| 7,132,659 | B2 | 11/2006 | Starta et al. |
| 7,132,762 | B2 | 11/2006 | Metlitzky et al. |
| 7,135,788 | B2 | 11/2006 | Metlitzky et al. |
| 7,204,335 | B2 | 4/2007 | Stewart et al. |
| 7,218,236 | B2 | 5/2007 | Mcmillin et al. |
| 7,222,006 | B2 | 5/2007 | Proefke et al. |
| 7,256,700 | B1 | 8/2007 | Ruocco et al. |
| 7,260,976 | B2 | 8/2007 | Colman et al. |
| 7,287,617 | B2 | 10/2007 | Mobley et al. |
| 7,299,890 | B2 | 11/2007 | Mobley et al. |
| 7,329,390 | B2 | 2/2008 | Chrzan et al. |
| 7,341,693 | B2 | 3/2008 | Der et al. |
| 7,351,954 | B2 | 4/2008 | Zhang et al. |
| 7,359,773 | B2 | 4/2008 | Simon et al. |
| 7,377,147 | B1 | 5/2008 | Scheffler et al. |
| 7,377,352 | B2 | 5/2008 | Mobley et al. |
| 7,400,258 | B2 | 7/2008 | Crespo et al. |
| 7,401,493 | B2 | 7/2008 | Forrest |
| 7,404,311 | B2 | 7/2008 | Guth et al. |
| 7,422,723 | B1 | 9/2008 | Betsill et al. |
| 7,451,852 | B2 | 11/2008 | Stewart et al. |
| 7,481,292 | B2 | 1/2009 | Mobley et al. |
| 7,483,805 | B2 | 1/2009 | Sparks et al. |
| 7,493,792 | B2 | 2/2009 | Bouchoux et al. |
| 7,493,793 | B2 | 2/2009 | Guth et al. |
| 7,519,326 | B2 | 4/2009 | Thomas et al. |
| 7,530,851 | B2 | 5/2009 | Parnis et al. |
| 7,541,192 | B2 | 6/2009 | Stock |
| 7,543,472 | B2 | 6/2009 | Crespo et al. |
| 7,547,997 | B1 | 6/2009 | Simunek et al. |
| 7,570,172 | B2 | 8/2009 | Kamiki |
| 7,603,887 | B2 | 10/2009 | Schlichte et al. |
| 7,658,255 | B2 | 2/2010 | Nordin |
| 7,743,647 | B1 | 6/2010 | Israel et al. |
| 7,797,982 | B2 | 9/2010 | Burke et al. |
| 7,823,681 | B2 | 11/2010 | Crespo et al. |
| 7,841,224 | B2 | 11/2010 | Son |
| 7,860,677 | B2 | 12/2010 | Artiuch |
| 7,895,878 | B1 | 3/2011 | Guth et al. |
| 7,934,577 | B2 | 5/2011 | Devries et al. |
| 8,001,825 | B2 | 8/2011 | Pugh et al. |
| 8,059,003 | B2 | 11/2011 | Roth |
| 8,078,334 | B2 | 12/2011 | Goodrich |
| 8,197,417 | B2 | 6/2012 | Howard et al. |
| 8,224,608 | B1 | 7/2012 | Son et al. |
| 8,240,419 | B2 | 8/2012 | Zimmermann et al. |
| 8,250,900 | B2 | 8/2012 | Son |
| 8,267,215 | B2 | 9/2012 | Ozaki |
| 8,311,858 | B2 | 11/2012 | Mcmillan et al. |
| 8,317,998 | B2 | 11/2012 | Pratt et al. |
| 8,326,484 | B2 | 12/2012 | McGarry et al. |

(56) References Cited

U.S. PATENT DOCUMENTS

| | | |
|---|---|---|
| 8,359,901 B2 | 1/2013 | Freund et al. |
| 8,364,431 B2 | 1/2013 | Russell et al. |
| 8,418,523 B2 | 4/2013 | Lueck et al. |
| 8,505,360 B2 | 8/2013 | Ruocco et al. |
| 8,515,704 B2 | 8/2013 | Son et al. |
| 8,667,829 B2 | 3/2014 | Guth et al. |
| 8,676,439 B2 | 3/2014 | Huang et al. |
| 8,688,073 B2 | 4/2014 | Peisa et al. |
| 8,701,815 B2 | 4/2014 | Polzius et al. |
| 8,713,985 B2 | 5/2014 | Lueck et al. |
| 8,718,536 B2 | 5/2014 | Hannon |
| 8,755,944 B2 | 6/2014 | Elliott et al. |
| D708,757 S | 7/2014 | Shibata |
| 8,795,187 B2 | 8/2014 | Morley et al. |
| 8,800,708 B2 | 8/2014 | Morley et al. |
| 8,822,929 B2 | 9/2014 | Nesa et al. |
| 8,918,251 B2 | 12/2014 | Tarnutzer et al. |
| 8,957,771 B2 | 2/2015 | Arringdale et al. |
| 9,020,773 B2 | 4/2015 | Son et al. |
| 9,026,267 B2 | 5/2015 | Macheca et al. |
| 9,103,818 B2 | 8/2015 | Son |
| 9,128,067 B2 | 9/2015 | Ostermann et al. |
| 9,128,137 B2 | 9/2015 | Troxler et al. |
| 9,129,336 B2 | 9/2015 | Ehrman et al. |
| 9,140,685 B2 | 9/2015 | Christman et al. |
| 9,165,131 B1 | 10/2015 | Kowalick |
| 9,196,441 B2 | 11/2015 | Wilson |
| 9,207,223 B2 | 12/2015 | Arias et al. |
| 9,221,339 B2 | 12/2015 | Comeau |
| 9,227,512 B2 | 1/2016 | Comeau et al. |
| 9,238,467 B1 | 1/2016 | Lambert et al. |
| 9,260,012 B2 | 2/2016 | Lopez et al. |
| 9,261,885 B2 | 2/2016 | Tryfonos et al. |
| 9,272,713 B1 | 3/2016 | Dvoskin |
| 9,278,696 B2 | 3/2016 | Yi et al. |
| 9,290,095 B2 | 3/2016 | Roth et al. |
| 9,290,174 B1 | 3/2016 | Zagorski et al. |
| 9,296,298 B2 | 3/2016 | Williams et al. |
| 9,308,892 B2 | 4/2016 | Schwarz et al. |
| 9,311,758 B2 | 4/2016 | Choi |
| 9,318,287 B2 | 4/2016 | Saito et al. |
| 9,324,224 B2 | 4/2016 | Schumacher |
| 9,326,713 B2 | 5/2016 | Bellehumeur et al. |
| 9,354,010 B1 | 5/2016 | Mcculloch |
| 9,371,056 B2 | 6/2016 | Lunstedt et al. |
| 9,376,017 B2 | 6/2016 | Bailey et al. |
| 9,417,232 B2 | 8/2016 | Keays et al. |
| 9,442,103 B1 | 9/2016 | Goad |
| 9,475,387 B2 | 10/2016 | Wu et al. |
| 9,475,459 B2 | 10/2016 | Tieman |
| 9,481,245 B2 | 11/2016 | Nelson et al. |
| 9,488,672 B2 | 11/2016 | Macdonald |
| 9,496,108 B2 | 11/2016 | Kawamura |
| 9,516,776 B2 | 12/2016 | Kawamura |
| 9,518,966 B2 | 12/2016 | Duric et al. |
| 9,552,681 B2 | 1/2017 | Burger et al. |
| 9,562,883 B2 | 2/2017 | Silverman et al. |
| 9,562,889 B2 | 2/2017 | Son et al. |
| 9,562,890 B2 | 2/2017 | Son |
| 9,630,497 B2 | 4/2017 | Quix et al. |
| 9,662,976 B2 | 5/2017 | Comeau et al. |
| 9,746,456 B2 | 8/2017 | Keays et al. |
| 9,770,984 B2 | 9/2017 | Comeau et al. |
| 9,772,318 B1 | 9/2017 | Lyon |
| 9,784,755 B2 | 10/2017 | Scheffler et al. |
| 10,040,349 B2 | 8/2018 | Devries et al. |
| 2001/0037070 A1 | 11/2001 | Cranley et al. |
| 2001/0040503 A1 | 11/2001 | Bishop et al. |
| 2002/0127145 A1 | 9/2002 | Der Ghazarian et al. |
| 2003/0000281 A1 | 1/2003 | Ketler et al. |
| 2003/0167821 A1 | 9/2003 | Sussman et al. |
| 2003/0176803 A1 | 9/2003 | Gollar et al. |
| 2003/0216660 A1 | 11/2003 | Ben-oren et al. |
| 2004/0055359 A1 | 3/2004 | Ketler et al. |
| 2004/0074279 A1 | 4/2004 | Forrest |
| 2004/0075538 A1 | 4/2004 | Flick et al. |
| 2004/0085211 A1 | 5/2004 | Gotfried et al. |
| 2004/0239510 A1 | 12/2004 | Karsten et al. |
| 2005/0000981 A1 | 1/2005 | Peng et al. |
| 2005/0031483 A1 | 2/2005 | Liu et al. |
| 2005/0273016 A1 | 12/2005 | Colman et al. |
| 2006/0081033 A1 | 4/2006 | Peng |
| 2006/0156789 A1 | 7/2006 | Frank et al. |
| 2006/0263254 A1 | 11/2006 | Lee |
| 2007/0044534 A1 | 3/2007 | Forrest et al. |
| 2007/0062249 A1 | 3/2007 | Forrest |
| 2007/0144812 A1 | 6/2007 | Stewart et al. |
| 2007/0239992 A1 | 10/2007 | White et al. |
| 2008/0106390 A1 | 5/2008 | White et al. |
| 2008/0154535 A1 | 6/2008 | Sparks et al. |
| 2008/0221743 A1 | 9/2008 | Schwarz et al. |
| 2008/0227466 A1 | 9/2008 | Rabanne et al. |
| 2009/0004054 A1 | 1/2009 | Burke et al. |
| 2009/0056408 A1 | 3/2009 | Tryfonos et al. |
| 2009/0153296 A1 | 6/2009 | Legasse et al. |
| 2009/0205407 A1 | 8/2009 | Marhefka et al. |
| 2009/0227887 A1 | 9/2009 | Howard et al. |
| 2010/0012417 A1 | 1/2010 | Walter et al. |
| 2010/0042333 A1 | 2/2010 | Scheffler et al. |
| 2010/0223975 A1 | 9/2010 | Lueck et al. |
| 2010/0314190 A1 | 12/2010 | Zimmermann et al. |
| 2011/0084820 A1 | 4/2011 | Walter et al. |
| 2011/0111700 A1 | 5/2011 | Hackett |
| 2011/0178420 A1 | 7/2011 | Ridder et al. |
| 2011/0283770 A1 | 11/2011 | Hok et al. |
| 2011/0292209 A1 | 12/2011 | Morley et al. |
| 2011/0309932 A1 | 12/2011 | Arringdale et al. |
| 2012/0050046 A1 | 3/2012 | Satorius et al. |
| 2012/0125076 A1 | 5/2012 | Tryfonos et al. |
| 2012/0209634 A1 | 8/2012 | Ling et al. |
| 2012/0291517 A1 | 11/2012 | Son et al. |
| 2012/0295456 A1 | 11/2012 | Severac et al. |
| 2012/0306618 A1 | 12/2012 | Tieman et al. |
| 2013/0074575 A1 | 3/2013 | Duric et al. |
| 2013/0155641 A1 | 6/2013 | Profeta et al. |
| 2013/0158838 A1 | 6/2013 | Yorke et al. |
| 2013/0203365 A1 | 8/2013 | Tieman et al. |
| 2013/0281873 A1 | 10/2013 | Evans et al. |
| 2013/0325924 A1 | 12/2013 | Moshfeghi |
| 2014/0041436 A1 | 2/2014 | Knott et al. |
| 2014/0048040 A1 | 2/2014 | Rivet et al. |
| 2014/0061043 A1 | 3/2014 | Stock et al. |
| 2014/0062722 A1 | 3/2014 | Ofir et al. |
| 2014/0076022 A1 | 3/2014 | Ohlsson et al. |
| 2014/0156111 A1 | 6/2014 | Ehrman et al. |
| 2014/0172467 A1* | 6/2014 | He .................. B60K 28/06 705/4 |
| 2014/0180500 A1 | 6/2014 | Hannon et al. |
| 2014/0229061 A1 | 8/2014 | Tarnutzer et al. |
| 2014/0230518 A1 | 8/2014 | Lueck et al. |
| 2014/0311214 A1 | 10/2014 | Wolf et al. |
| 2014/0358020 A1 | 12/2014 | Park et al. |
| 2015/0008063 A1 | 1/2015 | Walter et al. |
| 2015/0021113 A1 | 1/2015 | Lefevbre et al. |
| 2015/0066238 A1 | 3/2015 | Todd et al. |
| 2015/0066284 A1 | 3/2015 | Yopp |
| 2015/0070340 A1 | 3/2015 | Trachtenberg et al. |
| 2015/0081134 A1 | 3/2015 | Burger |
| 2015/0094080 A1 | 4/2015 | Bleecher Snyder et al. |
| 2015/0160190 A1 | 6/2015 | Ravishankar |
| 2015/0164416 A1 | 6/2015 | Nothacker et al. |
| 2015/0183386 A1 | 7/2015 | Tieman |
| 2015/0187147 A1 | 7/2015 | Tieman |
| 2015/0197151 A1 | 7/2015 | Ballard |
| 2015/0222349 A1 | 8/2015 | Sloan et al. |
| 2015/0228437 A1 | 8/2015 | Didimo et al. |
| 2015/0244452 A1 | 8/2015 | Grohman et al. |
| 2015/0251660 A1 | 9/2015 | Nelson |
| 2015/0289295 A1 | 10/2015 | Granbery |
| 2015/0297117 A1 | 10/2015 | Park et al. |
| 2015/0365986 A1 | 12/2015 | Lee et al. |
| 2016/0003746 A1 | 1/2016 | Mccrary et al. |
| 2016/0016467 A1 | 1/2016 | Mathissen et al. |
| 2016/0054296 A1 | 2/2016 | Son |

(56) References Cited

U.S. PATENT DOCUMENTS

| | | | |
|---|---|---|---|
| 2016/0065298 A1 | 3/2016 | Nakagawa et al. |
| 2016/0082837 A1 | 3/2016 | Comeau et al. |
| 2016/0086021 A1 | 3/2016 | Grohman et al. |
| 2016/0089976 A1 | 3/2016 | Comeau |
| 2016/0096531 A1 | 4/2016 | Hoye |
| 2016/0101727 A1 | 4/2016 | Kwon |
| 2016/0123955 A1 | 5/2016 | Wolf, Jr. |
| 2016/0137164 A1 | 5/2016 | Jones |
| 2016/0153963 A1 | 6/2016 | Keays |
| 2016/0185217 A1 | 6/2016 | Hannon |
| 2016/0188964 A1 | 6/2016 | Quddus et al. |
| 2016/0207398 A1 | 7/2016 | Lopez et al. |
| 2016/0229413 A1 | 8/2016 | Morley et al. |
| 2016/0240064 A1 | 8/2016 | Schumacher |
| 2016/0252492 A1 | 9/2016 | Rarama et al. |
| 2016/0272153 A1 | 9/2016 | Doi et al. |
| 2016/0272214 A1 | 9/2016 | Chen |
| 2016/0280230 A1 | 9/2016 | Hsieh |
| 2016/0288741 A1 | 10/2016 | Shafer |
| 2016/0303967 A1 | 10/2016 | Quix et al. |
| 2016/0318521 A1* | 11/2016 | Nothacker ............ B60W 40/08 |
| 2016/0327541 A1 | 11/2016 | Reinstaedtler |
| 2016/0349239 A1 | 12/2016 | Chien |
| 2016/0358029 A1 | 12/2016 | Mullin |
| 2016/0377597 A1 | 12/2016 | Tschuncky et al. |
| 2017/0005718 A1 | 1/2017 | Sloan et al. |
| 2017/0006151 A1 | 1/2017 | Doorandish |
| 2017/0035332 A1 | 2/2017 | Wahnschafft |
| 2017/0036621 A1 | 2/2017 | Tieman |
| 2017/0050518 A1 | 2/2017 | Ver Steeg et al. |
| 2017/0050519 A1 | 2/2017 | Cristofaro |
| 2017/0057353 A1 | 3/2017 | Griffin |
| 2017/0096145 A1 | 4/2017 | Bahn |
| 2017/0096146 A1 | 4/2017 | Jones |
| 2017/0101006 A1 | 4/2017 | Devries et al. |
| 2017/0101007 A1 | 4/2017 | Devries et al. |
| 2017/0104865 A1* | 4/2017 | Skelton ................ H04B 1/3822 |
| 2017/0131261 A1 | 5/2017 | Biondo et al. |
| 2017/0282712 A1 | 10/2017 | Devries et al. |
| 2017/0282713 A1 | 10/2017 | Devries et al. |
| 2017/0316621 A1 | 11/2017 | Jefferies et al. |
| 2017/0346688 A1 | 11/2017 | Reddy et al. |
| 2018/0011068 A1 | 1/2018 | Lyon |
| 2018/0027144 A1 | 1/2018 | Yokoyama |
| 2018/0074029 A1 | 3/2018 | Devries et al. |
| 2018/0074030 A1 | 3/2018 | Devries et al. |
| 2018/0091930 A1* | 3/2018 | Jefferies ................ H04L 67/125 |
| 2018/0150061 A1 | 5/2018 | Yang et al. |
| 2019/0072531 A1 | 3/2019 | Devries et al. |
| 2019/0076056 A1 | 3/2019 | Carlson et al. |
| 2019/0092342 A1* | 3/2019 | Biondo ................ A61B 5/4845 |
| 2019/0126935 A1* | 5/2019 | Phillips ............ B60W 50/0098 |
| 2019/0145956 A1 | 5/2019 | Lyon |

FOREIGN PATENT DOCUMENTS

| | | |
|---|---|---|
| CA | 1337463 | 10/1995 |
| CA | 2269546 | 4/1998 |
| CA | 2270809 | 10/1999 |
| CA | 2731040 | 1/2010 |
| CA | 2711410 | 1/2012 |
| CA | 2788785 | 2/2013 |
| CA | 2780135 | 12/2013 |
| CA | 2821197 | 1/2015 |
| CA | 2858708 | 2/2015 |
| CA | 2905093 | 9/2015 |
| CA | 2684266 | 3/2017 |
| CA | 2938417 | 4/2018 |
| CA | 2938407 | 7/2018 |
| CN | 102397616 | 4/2012 |
| CN | 102778541 | 11/2012 |
| CN | 102955472 | 3/2013 |
| CN | 101821120 | 11/2013 |
| CN | 103578853 | 2/2014 |
| CN | 105699296 | 6/2016 |
| DE | 19638971 | 4/1998 |
| DE | 10238094 | 3/2004 |
| DE | 102007029271 | 12/2008 |
| DE | 102013015826 | 3/2015 |
| DE | 102013018663 | 5/2015 |
| DE | 10350178 | 11/2016 |
| DE | 202015009104 | 11/2016 |
| EP | 243470 | 11/1987 |
| EP | 516623 | 8/1995 |
| EP | 1591296 | 11/2005 |
| EP | 1933218 | 6/2008 |
| EP | 1987355 | 2/2012 |
| EP | 2127599 | 3/2012 |
| EP | 2544000 | 1/2013 |
| EP | 2623378 | 8/2013 |
| EP | 2808681 | 12/2014 |
| EP | 2760041 | 9/2015 |
| EP | 2740252 | 4/2016 |
| EP | 3018476 | 5/2016 |
| EP | 2360048 | 9/2016 |
| EP | 2867666 | 10/2016 |
| EP | 2761267 | 11/2016 |
| EP | 3091489 | 11/2016 |
| EP | 3156276 | 4/2017 |
| EP | 3156277 | 4/2017 |
| EP | 3116736 | 7/2019 |
| ES | 2660013 | 3/2018 |
| FR | 2535143 | 4/1984 |
| FR | 3033149 | 9/2016 |
| GB | 2049193 | 12/1980 |
| GB | 2313198 | 11/1997 |
| GB | 2536422 | 9/2016 |
| IN | 201102479 | 12/2011 |
| KR | 20100070199 | 6/2010 |
| KR | 20100072578 | 7/2010 |
| KR | 101059978 | 8/2011 |
| KR | 1020160068277 | 6/2016 |
| KR | 1020160096251 | 8/2016 |
| TW | 565696 | 12/2003 |
| WO | 8702773 | 5/1987 |
| WO | 8702832 | 5/1987 |
| WO | 9212416 | 7/1992 |
| WO | 9422686 | 10/1994 |
| WO | 1994022686 | 10/1994 |
| WO | 9641428 | 12/1996 |
| WO | 9714947 | 4/1997 |
| WO | 1998027416 | 6/1998 |
| WO | 2001075439 | 10/2001 |
| WO | 2001086286 | 11/2001 |
| WO | 2002048705 | 6/2002 |
| WO | 2002085706 | 10/2002 |
| WO | 2005028788 | 3/2005 |
| WO | 2007059263 | 5/2007 |
| WO | 2007094712 | 8/2007 |
| WO | 2008073029 | 6/2008 |
| WO | 2009067064 | 5/2009 |
| WO | 2009111484 | 9/2009 |
| WO | 2009155048 | 12/2009 |
| WO | 2010009406 | 4/2010 |
| WO | 2010086557 | 8/2010 |
| WO | 2010093317 | 8/2010 |
| WO | 2010094967 | 8/2010 |
| WO | 2010025478 | 3/2011 |
| WO | 2011143693 | 11/2011 |
| WO | 2012041505 | 4/2012 |
| WO | 2012122385 | 12/2012 |
| WO | 2013001265 | 1/2013 |
| WO | 2013023032 | 2/2013 |
| WO | 2013033099 | 3/2013 |
| WO | 2013051992 | 4/2013 |
| WO | 2013134460 | 9/2013 |
| WO | 2013191634 | 12/2013 |
| WO | 2014036088 | 3/2014 |
| WO | 2014134252 | 9/2014 |
| WO | 2015100166 | 7/2015 |
| WO | 2015116821 | 8/2015 |
| WO | 2015126867 | 8/2015 |
| WO | 2016009058 | 1/2016 |
| WO | 2016044926 | 3/2016 |

(56) References Cited

FOREIGN PATENT DOCUMENTS

| WO | 2016081905 | 5/2016 |
|---|---|---|
| WO | 2016092796 | 6/2016 |
| WO | 2016113353 | 7/2016 |
| WO | 2016137246 | 9/2016 |
| WO | 2016144738 | 9/2016 |
| WO | 2016170534 | 10/2016 |
| WO | 2016187243 | 11/2016 |
| WO | 2016193519 | 12/2016 |
| WO | 2017041482 | 3/2017 |
| WO | 2017064023 | 4/2017 |

OTHER PUBLICATIONS

"Final Office Action," for U.S. Appl. No. 15/621,507 dated Feb. 7, 2018 (30 pages).
"Non-Final Office Action," for U.S. Appl. No. 15/223,894 dated Jul. 28, 2017 (17 pages).
"Non-Final Office Action," for U.S. Appl. No. 15/621,507 dated Jul. 28, 2017 (14 pages).
"Non-Final Office Action," for U.S. Appl. No. 15/622,309 dated Aug. 7, 2017 (8 pages).
"Non-Final Office Action," for U.S. Appl. No. 15/622,309 dated Dec. 18, 2017 (15 pages).
"Non-Final Office Action," for U.S. Appl. No. 15/622,309 dated May 10, 2018 (11 pages).
"Non-Final Office Action," for U.S. Appl. No. 15/622,309 dated Nov. 13, 2018 (15 pages).
"Notice of Allowance," for U.S. Appl. No. 15/621,507 dated Apr. 17, 2018 (11 pages).
"Response to Final Office Action," for U.S. Appl. No. 15/223,894, filed on May 1, 2018 (13 pages).
"Response to Final Office Action," for U.S. Appl. No. 15/621,507, filed on Mar. 22, 2018 (10 pages).
"Response to Non Final Office Action," for U.S. Appl. No. 15/622,309, filed on Mar. 15, 2018 (15 pages).
"Response to Non Final Office Action," for U.S. Appl. No. 15/622,309, filed on Sep. 10, 2018 (10 pages).
Response to Non-Final Office Action dated Jul. 28, 2017, for U.S. Appl. No. 15/223,894, submitted via EFS-Web on Jan. 25, 2018, 11 pages.
"Response to Non-Final Office Action," for U.S. Appl. No. 15/621,507 (our file 365.0001 USC1) filed Oct. 27, 2017, 19 pages.
"Response to Non-Final Office Action," for U.S. Appl. No. 15/622,309 filed Nov. 7, 2017, 11 pages.
"Smart START IN-HOM User Instructions," SmartStartInc.com, Oct. 2009, 2 pages.
Voyomotive, Llc, "What is Voyo?," Product description retrieved on Oct. 9, 2015 from http://voyomotive.com/what-is-voyo/.
"EESR Response," for European Patent Application No. 16183848.7 filed with the EPO Oct. 16, 2017 (24 pages).
"Examiner's Report," for Canadian Patent Application No. 2,938,407 dated Sep. 20, 2017 (3 pages).
"Examiner's Report," for Canadian Patent Application No. 2,938,417 dated Jul. 12, 2017 (4 pages).
"Extended European Search Report," for European Patent Application No. 16183848.7 dated Mar. 14, 2017 (10 pages).
"Extended European Search Report," for European Patent Application No. 16183858.6 dated Mar. 14, 2017 (9 pages).
Mayer, R. "Ignition interlocks—A toolkit for program administrators, policymakers, and stakeholders," 2nd Edition. Report No. DOT TH 811 883, Feb. 2014, Washington, D.C.: National Highway Traffic Safety Administration (60 pages).
"Response to Examiner's Report," for Canadian Patent Application No. 2,938,407 filed with CIPO Dec. 19, 2017 (6 pages).
"Response to Examiner's Report," for Canadian Patent Application No. 2,938,417 filed with CIPO Aug. 24, 2017 (4 pages).
"Response to Extended European Search Report," for European Patent Application No. 16183858.6 filed with the EPO Oct. 12, 2017 (23 pages).

"ACS Alcosim Calibration Bench Multi Stage Breath Alcohol Simulator," https://acs-corp.com/image/brochures/20171208-BRO-ACS-CA-ENG-A5-ALCOSIMCalibrationBench-WEB.pdf Dec. 8, 2017, 2 pages.
"ACS Metrological Test Bench Multi Stage Breath Alcohol Simulator," https://acs-corp.com/image/brochures/20180129-BRO-ACS-CA-ENG-A5-MetrologicalTestBench-Web.pdf Jan. 29, 2018, 2 pages.
"Alcolizer Technology Industry Welcome to the AOD Industry Presentation," http://transafewa.com.au/wp-content/uploads/2014/11/Alcolizer-Technology-Industry-Presentation-JY-1509.pdf available at least as early as Mar. 20, 2015, 20 pages.
"Guardian Interlock Product WR3 Calibration Station," https://www.guardianinterlock.com.au/product/wr3-calibration-station Available at least as early as Mar. 11, 2015, 3 pages.
"Honeywell Biosystems Toxi IQ Express Docking Station ToxiPro Single Gas Detectors," https://www.brandtinst.com/biosystems/detector/IQExpress/index.html available at least as early as Jan. 20, 2008, 3 pages.
"Honeywell IQ Management System," https://www.honeywellanalytics.com/en/products/IQ-Management-System available at least as early as Oct. 18, 2014, 3 pages.
"RKI Instruments Docking and Callibration Station Gas Detection for Live SDM-E2," https://www.rkiinstruments.com/pdf/sdme2.pdf available at least as early as Mar. 29, 2014, 2 pages.
Semedo, Daniela "Rapid Breath Test Patented for Potential Quick Diagnosis of TB and Other Lung Diseases," Lung Disease News https://lungdiseasenews.com/2016/01/13/rapid-diagnostic-test-takes-on-tuberculosis-and-other-deadly-diseases/ Jan. 13, 2016, 8 pages.
"Where Did the Ignition Interlock Device Come From? A History," https://www.smartstartinc.com/blog/history-ignition-interlock-device/ Aug. 15, 2017, 8 pages.
"Accuracy Check Methods Webpage," Intoximeters, Inc., 2013, available as early as Jan. 29, 2013 (1 page).
"Alcolizer LE Main Web Page," Alcolizer Pty Ltd, www.alcolizer.com, available as early as Mar. 20, 2012 (2 pages).
"Alcolizer Re-Calibration Web Page," Alcolizer Pty Ltd, www.alcolizer.com/products/re-calibration, available as early as Mar. 20, 2012 (2 pages).
"Alcolizer Wall Mount Product Page," Alcolizer Pty Ltd, www.alcolizer.com/products/alcolizer-wm-wall-mount-series, available as early as Mar. 20, 2012 (2 pages).
"Alco-Sensor FST Operators Manual," Intoximeters, Inc., printed Jun. 2007 (37 pages).
"Alco-Sensor FST(R) Product Webpage," Intoximeters, Inc., available as early as Dec. 2, 2011 (2 pages).
"Alert J4X.ec Breath Alcohol Tester User Guide," Alcohol Countermeasure Systems, 2008 (36 pages).
"AutoRAE 2 Automatic Test and Calibration System Datasheet," RAE Systems, Inc., DS-1083-02, date unavailable (2 pages).
"AutoRAE 2 Automatic Test and Calibration System User's Guide," RAE Systems by Honeywell, Rev. E, Apr. 2014 (118 pages).
"AutoRAE Lite for QRAE II User's Guide," Rae Systems by Honeywell, Rev. A. Jun. 2009 (55 pages).
"Benefits of Alcosystems iBAC Solution," iBac Alcosystems AB, available online as early as Jan. 11, 2012 (2 pages).
"Bid Specifications: Galaxy(TM) Automated Test System," Mine Safety Appliances Company, available as early as Jul. 11, 2012 (4 pages).
"Breath Alcohol Testing Calibration Equipment Webpage," Intoximeters, Inc., www.intox.com/c-18-calibration.aspx, available as early as Feb. 13, 2012 (2 pages).
"Calibration Device and Method for Calibrating an Ignition Interlock Device," U.S. Appl. No. 14/706,402 as filed on May 7, 2015 (36 pages).
"Calibration Station for the Ventis™ MX4: Product Manual," Industrial Scientific Corporation, 2010 (40 pages).
"Calibration Station or Docking Station: Which one do you need for your gas detectors?," Industrial Scientific Corporation, 2015 (8 pages).
Comeau, Felix J. "Ignition Interlock Devices Support Program Development," Alcohol, Drugs and Traffic Safety—T 2000: Proceedings of the 15th International Conference on Alcohol, Drugs and Traffic Safety 2000 (5 pages).

(56) References Cited

OTHER PUBLICATIONS

"Communication Pursuant to Article 94(3) EPC," for European Patent Application No. 16183848.7 dated May 6, 2019 (6 pages).
"Communication Pursuant to Article 94(3) EPC," for European Patent Application No. 16183858.6 dated May 10, 2019 (6 pages).
"Description of Calibration Kiosk used for Intoxalock Breath Alcohol Detectors," Intoxalock Description as early as Jan. 2011, 4 pages.
"Draeger Gas Detection Product Brochure," Draeger Safety, Inc, 2009 (50 pages).
"Draeger Interlock(R) XT Product Webpage," Draeger Safety, Inc, www.draeger.us/sites/enus_us/Pages/Law-Enforcement/INTERLOCK-XT.aspx?navID=173, available as early as Apr. 26, 2012 (2 pages).
"Draeger Introduces X-Dock, a Test and Calibration Station for Portable Gas Detection," Press Release, Draeger Safety, Inc., Apr. 23, 2013 (2 pages).
"Draeger Product Selector Webpage," Draeger Safety, Inc, http://www.draeger.us/sites/enus_us/Pages/Law Enforcement/ProductSelector.aspx?navID=159, available as early as Apr. 26, 2012 (2 pages).
"Draeger X-am 2500 Technical Manual," Draeger Safety, Inc, Nov. 2012 (36 pages).
"Draeger X-dock 5300, 6300/6600 Technical Manual," Draeger Safety, Inc., Aug. 2013 (28 pages).
"Draeger X-Dock 5300/6300/6600 Product Brochure," Draeger Safety, Inc, 2012 (5 pages).
"Dry Gas Standard Webpage," Intoximeters, Inc., www.intox.com/t-DryGasStandard.aspx, available as early as Jan. 29, 2013 (2 pages).
"Ds2: Administrator's Guide to the DS2 Docking Station," Industrial Scientific Corporation, Nov. 11, 2008 (261 pages).
"Final Office Action," for U.S. Appl. No. 15/261,231 dated Jan. 14, 2019 (10 pages).
"Final Office Action," for U.S. Appl. No. 15/261,253 dated Mar. 7, 2019 (17 pages).
"Galaxy (R) GX2 Automated Test System Quick Start Guide—Description and Setup," Mine Safety Appliances Company, Sep. 2012 (10 pages).
"Galaxy GX2 Automated Test System Frequently Asked Questions," Mine Safety Appliances Company, Published Aug. 2012 (1 page).
"Galaxy(R) Automated Test System Operating Manual," Mine Safety Appliances Company 2008, available online as early as Jul. 11, 2012 (124 pages).
"Galaxy(R) Automated Test System Product Brochure," Mine Safety Appliances Company, Sep. 2011 (4 pages).
"Galaxy(R) GX2—Simplicity Counts," Product Brochure, Mine Safety Appliances, Aug. 2012 (2 pages).
"Galaxy(R) GX2 Automated Test System Datasheet," Mine Safety Appliances Company, published Aug. 2012 (6 pages).
"Galaxy(R) GX2 Automated Test System Operating Manual," Mine Safety Appliances Company 2012 (72 pages).
"Galaxy(R) Network Interface and Network Manager Instruction Manual," Mine Safety Appliances Company 2010, available online as early as Jul. 11, 2012 (69 pages).
"Highway Safety Programs; Conforming Products List of Calibrating Units for Breath Alcohol Testers," Department of Transportation National Highway Traffic Safety Administration. Federal Register / vol. 77, No. 204 / Monday, Oct. 22, 2012 (3 pages).
"Highway Safety Programs; Model Specifications for Calibrating Units for Breath Alcohol Testers; Conforming Products List of Calibrating Units for Breath Alcohol Testers," Federal Register, vol. 72, No. 121 (Jun. 25, 2007) (7 pages).
"Highway Safety Programs; Model Specifications for Calibrating Units for Breath Alcohol Testers; Conforming Products List of Calibrating Units," Federal Register, vol. 62, No. 156 (Aug. 13, 1997) (10 pages).
Hök, Bertil et al., "Breath Analyzer for Alcolocks and Screening Devices," IEEE Sensors Journal, vol. 10, No. 1, 10-15, Jan. 2010 (6 pages).
"iBAC Product Brochure," iBac Alcosystems AB, 2011 (6 pages).

"Interlock Help Webpage," Alcohol Countermeasure Systems (International), Inc., www.interlockhelp.com, available as early as Dec. 27, 2011 (1 page).
"Intox DMT Product Brochure," Intoximeters, Inc., printed May 2019 (2 pages).
"Intox EC/IR II Training Materials," Intoximeters Inc. Feb. 22-25, 2010, published Jun. 29, 2009 pp. 1-240.
"Intox EC/IR(R) II Webpage," Intoximeters, Inc., www.intox.com/p-562-intox-ecir-ii.aspx, available as early as Sep. 21, 2011 (1 page).
"Intoxilyzer 8000 Reference Guide," Florida Department of Law Enforcement Alcohol Testing Program, Feb. 2006 (14 pages).
"Intoxilyzer 9000 Brochure," CMI, Inc., available at least as early as Feb. 1, 2015 as shown on the Way Back Machine available online., 2 pages.
Jonsson, A. et al., "Development of a Breath Alcohol Analyzer for Use on Patients in Emergency Care," Dössel O., Schlegel W.C. (eds) World Congress on Medical Physics and Biomedical Engineering, Sep. 7-12, 2009 (4 pages).
"LifeSafer Ignition Interlock Webpage," LifeSafer, www.lifesafer.com/, available as early as Jul. 19, 2012 (3 pages).
"Lion Alcometer(R) 500 User Handbook," Lion Laboratories Limited, 2011 (54 pages).
"Method for Calibrating an Ignition Interlock Device," U.S. Appl. No. 14/036,343 as filed on Sep. 25, 2013 (31 pages).
"MicroDock II Automatic Test and Calibration Station User Manual," BW Technologies by Honeywell, 2009 (101 pages).
"Non-Final Office Action," for U.S. Appl. No. 15/261,231 dated Jul. 8, 2019 (8 pages).
"Non-Final Office Action," for U.S. Appl. No. 15/261,231 dated Sep. 14, 2018 (21 pages).
"Non-Final Office Action," for U.S. Appl. No. 15/261,253 dated Aug. 9, 2018 (27 pages).
"Operating the DataMaster DMT," Version 1.0, Division of Criminal Investigation, Alcohol Section, Jul. 2009 (163 pages).
"Response to Final Office Action," for U.S. Appl. No. 15/261,231, filed on Jun. 14, 2019 (9 pages).
"Response to Final Office Action," for U.S. Appl. No. 15/261,253, filed on Sep. 9, 2019 (14 pages).
"Response to Non Final Office Action," for U.S. Appl. No. 15/261,231, filed on Nov. 7, 2018 (11 pages).
"Response to Non Final Office Action," for U.S. Appl. No. 15/261,253, filed on Nov. 2, 2018 (10 pages).
"Sdm-2012 Docking Station Standalone Configuration Operator's Manual," RKI Instruments, released Aug. 12, 2013 (112 pages).
"Smart Start IN-HOM User Instructions," SmartStartInc.com, Believed to have been published at least as early as Aug. 2010 (2 pages).
"Solaris(R) MultiGas Detector Operating Manual," Mine Safety Appliances Company 2007 (162 pages).
"Tim(R) Total Instrument Manager Instruction Manual," Mine Safety Appliances Company 2002 (87 pages).
"True-Cal II Product Webpage," Intoximeters, Inc., http://www.intox.com/p-723-true-cal-ii.aspx, available as early as Sep. 15, 2013 (1 page).
"TruTouch Technologies FAQ Webpage," TruTouch Technologies Inc., www.tttinc.com/FAQ.php, available as early as Dec. 22, 2012 (4 pages).
"TruTouch Technologies Webpage," TruTouch Technologies Inc., www.tttinc.com, available as early as May 19, 2012 (1 page).
Van Tassel, William E. "An Evaluation of Pocket-Model, Numerical Readout Breath Alcohol Testing Instruments," Dissertation Submitted to Texas A&M University, Aug. 2003 (164 pages).
Wood, Chris "Breathometer Turns Your Smartphone Into a Breathalyzer," New Atlas, https://newatlas.com/breathometer-smartphone-breathalyzer/26634/, Mar. 13, 2013 (4 pages).
"Response to Communication Pursuant to Article 94(3) EPC," for European Patent Application No. 16183848.7 filed Nov. 14, 2019 (13 pages).

* cited by examiner

NETWORKED INTOXICATION VEHICLE IMMOBILIZATION

This application claims the benefit of pending U.S. Nonprovisional application Ser. No. 15/223,921, filed Jul. 29, 2016, as a continuation, which claims the benefit of U.S. Provisional Application No. 62/240,978, filed Oct. 13, 2015, U.S. Provisional Application No. 62/266,279, filed Dec. 11, 2015 and U.S. Provisional Application No. 62/306,177, filed Mar. 10, 2016, the contents of which are herein incorporated by reference.

FIELD

The invention relates generally to vehicle immobilization in response to intoxication of a driver, and more specifically to networked vehicle intoxication immobilization.

BACKGROUND

Vehicles incorporate breath alcohol ignition interlock devices, sometimes abbreviated as BAIIDs, to prevent a driver with a known history of driving while intoxicated with alcohol from operating the vehicle while intoxicated. Such devices are designed to prevent a driver from starting a motor vehicle when the driver's breath alcohol concentration (BAC) is at or above a set alcohol concentration. Each state in the U.S. has adopted a law providing for use of such BAIID devices as a sanction for drivers convicted of driving while intoxicated, or as a condition of restoring some driving privileges after such offenses.

A typical BAIID device meets guidelines established by the National Highway Traffic Safety Administration (NHTSA) in published model specifications for BAIIDs, which specify various features and safeguards that should be present in such a device to make it an effective and reliable deterrent to intoxicated driving. For example, the model specifies a volume of air in a breath that the driver provides to ensure that an adequate volume of air to ensure an accurate result is provided, and specifies how such a device should be installed into a vehicle to prevent the vehicle from operating pending a determination that the driver is not intoxicated. Most state programs and manufacturer BAIID products adhere to the NHTSA model guidelines, providing a uniform market for various brands of BAIID products.

In operation, a driver must use a BAIID device by blowing into an alcohol-sensing element such as a fuel cell that measures the amount of alcohol in the driver's breath, thereby providing a reliable estimate of the blood alcohol concentration in the driver's blood. The BAIID reads a signal from the fuel cell or other alcohol-sensing element, and determines whether the driver's blood alcohol content exceeds a threshold amount. If the driver's blood alcohol content does not exceed the threshold, the driver is determined not to be intoxicated and the BAIID allows the vehicle to start and run by electrically enabling a system within the vehicle, such as the starter, fuel pump, ignition, or the like. If the driver is intoxicated, the vehicle is not allowed to start, and the BAIID device records a violation.

The BAIID system is installed in the driver's vehicle as a consequence of a previous conviction for driving while intoxicated, as a condition of having some driving privileges restored. Because the security and integrity of the BAIID is important to ensuring compliance from the convicted intoxicated driver and to ensuring safety of others on the road, the system design and installation are desirably configured to make circumventing the BAIID to operate the vehicle while intoxicated both readily detectable and somewhat difficult. This is achieved in most systems by hard-wiring the BAIID system into the car's electrical system, including various connections to disable the vehicle's starter, fuel pump, ignition, or other elements critical to the vehicle's operation, and by connecting the BAIID such that it can monitor the car's operation to ensure that unauthorized operation is not taking place.

Installation therefore typically involves wiring multiple connections from the BAIID device in the passenger compartment of a car to various electrical systems within the car, such as a starter or fuel pump in the engine compartment, and speed sensor or mileage sensor connections in the car's dashboard. This usually requires removing at least part of the dashboard, routing wires through the firewall into the engine compartment, and connecting wires to various electrical system components in the vehicle's dashboard systems. Further, installation varies significantly by type of vehicle, making the installation process more difficult and time-consuming. This results in significant cost to perform such an installation, and typically results in permanent damage to the vehicle such as where holes are cut in the vehicle to run wires, wires are cut and spliced, and components of the BAIID system are mounted to the vehicle.

Because installation of BAIID devices is complex, expensive, time-consuming, and often results in permanent vehicle damage, it is desirable to provide an effective BAIID system with simpler and less intrusive installation.

SUMMARY

One example embodiment comprises a vehicle immobilization system, including a detection element operable to detect a level of an intoxicant in a user's breath. A control module is operable to receive a signal from the detection element indicating the level of intoxicant in the user's breath, and to selectively restrict operation of a vehicle based on the level of intoxicant in the user's breath exceeding a threshold. A relay is operable to replace a relay in the vehicle, and to wirelessly communicate with the control module such that the control module is operable to control the relay to selectively restrict operation of the vehicle.

In a further example, the relay is operable to communicate with the control module via a bidirectional Bluetooth wireless connection, and to control operation of at least one of a fuel pump, a starter motor, a governor, or an ignition of the vehicle.

In another example, the relay is operable to communicate its state to the control module, and the relay is operable to selectively restrict operation of the vehicle if it is not in communication with the control module.

In another example, a vehicle immobilization system includes a detection element operable to detect a level of an intoxicant in a user's breath, and a control module operable to receive a signal from the detection element indicating the level of intoxicant in the user's breath. The control module is also operable to selectively restrict operation of the vehicle based on the level of intoxicant in the user's breath exceeding a threshold. The control module achieves this in various examples by selectively disrupting at least one communications bus within the vehicle via a connection between the control module and the communications bus using an Onboard Diagnostic (OBD) port of the vehicle to selectively restrict operation of the vehicle, or by selectively overwriting at least a portion of a firmware within the vehicle via a connection between the control module and the communications bus using an Onboard Diagnostic (OBD) port of the vehicle to selectively restrict operation of the vehicle.

The details of one or more examples of the invention are set forth in the accompanying drawings and the description below. Other features and advantages will be apparent from the description and drawings, and from the claims.

DETAILED DESCRIPTION

Figure 1:
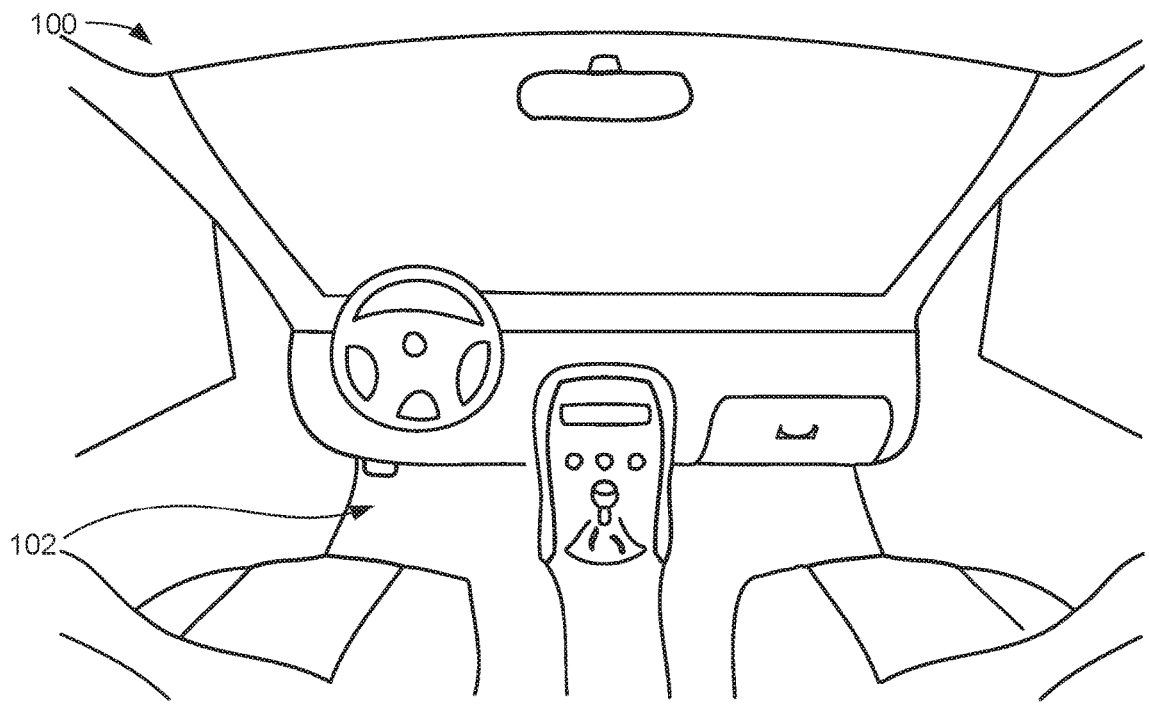
FIG. 1 shows a part of a vehicle interior as may be used to practice some examples.

In the following detailed description of example embodiments, reference is made to specific example embodiments by way of drawings and illustrations. These examples are described in sufficient detail to enable those skilled in the art to practice what is described, and serve to illustrate how elements of these examples may be applied to various purposes or embodiments. Other embodiments exist, and logical, mechanical, electrical, and other changes may be made.

Features or limitations of various embodiments described herein, however important to the example embodiments in which they are incorporated, do not limit other embodiments, and any reference to the elements, operation, and application of the examples serve only to define these example embodiments. Features or elements shown in various examples described herein can be combined in ways other than shown in the examples, and any such combinations are explicitly contemplated to be within the scope of the examples presented here. The following detailed description does not, therefore, limit the scope of what is claimed.

Breath alcohol ignition interlock devices, also known as BAIIDs, are commonly installed in vehicles to prevent a driver with a history of driving while intoxicated from starting a motor vehicle when the driver's breath alcohol concentration (BAC) is at or above a set alcohol concentration. Concentration of alcohol in a driver's breath is closely proportional to the concentration of alcohol in the driver's blood, which is typically the basis upon which intoxication is legally determined. Because a driver must blow into an alcohol-sensing element of a BAIID such as a fuel cell that measures the amount of alcohol in the driver's breath before the BAIID enables normal car operation, the BAIID can effectively prevent intoxicated drivers from driving a vehicle while intoxicated by selectively disabling the vehicle based on successful completion of the required BAIID test.

The BAIID system is also desirably equipped to monitor for attempts to defeat the device, such as shorting the starter wires selectively interrupted by the BAIID device or otherwise enabling vehicle operation by circumventing the BAIID. This is achieved in some examples by hard-wiring the BAIID to both the starter or other vehicle element and to vehicle instrumentation to detect operation or movement of the vehicle, such that unauthorized operation of the vehicle can be detected and recorded. The greater the amount of such vehicle information is available to the BAIID system, the more difficult it may be to defeat the BAIID device without the defeat attempt being detected and recorded as a violation. Installation of such a system typically therefore includes hard-wiring the BAIID system into the car's electrical system at several locations, including connections to disable the vehicle's starter, fuel pump, ignition, or other elements critical to the vehicle's operation, and including connecting the BAIID to vehicle instrumentation such that it can monitor the car's operation to ensure that unauthorized operation is not taking place.

But, connecting the BAIID device to several different systems associated with the engine and dash instrumentation of the vehicle typically involves routing wires from the BAIID device in the passenger compartment of a car to one or more systems within the engine compartment such as a starter or fuel pump, and to one or more instrumentation systems such as the speedometer, odometer, or other such dashboard instrumentation. Although installation can vary significantly from vehicle to vehicle, a typical process therefore involves determining a preferred installation plan for the particular vehicle, removing part of all of the dash, drilling a hole through the firewall to access the engine compartment, and routing and securing wiring harnesses to each system to be controlled or monitored by the BAIID. The time and cost to install the BAIID device therefore often runs into hundreds or thousands of dollars, and many hours' work. Further, the installation typically results in permanent damage to the vehicle, as it involves cutting holes in the vehicle to run wires, cutting and splicing wires, and attaching components of the BAIID system such as the wiring harness and a mount for the handheld detection unit to the vehicle.

Some examples described herein therefore provide for BAIID systems or devices having improved functionality, cost, installation time, installation cost, and installation damage to the vehicle, as described herein. This is achieved in various examples by various combinations of vehicle monitoring and control using the vehicle's on-board diagnostic port and a wireless relay, such as by using a data link connector commonly referred to as an OBDII port to monitor vehicle operational data and/or control the vehicle's operation, and by using a wireless relay to control the vehicle's operation and/or monitor the state of one or more vehicle systems.

FIG. 1 shows a portion of an interior of a vehicle as may be used to practice some examples. Here, the interior of a car 100 includes a driver's seat on the left, a front passenger seat on the right, a steering wheel, and other common elements of a typical car interior. The vehicle further includes a standard data link connector, commonly called an On-Board Diagnostic connector as shown at 102. A data link connector such as the on On-Board Diagnostic (OBD) connector is a connector that provides access to a system that gives access to information about the status of a number of vehicle sub-systems. In other examples, the data link connector will provide access to other vehicle systems, such as manufacturer-proprietary vehicle systems or networks. The most recent versions of OBD connectors are standardized digital communications ports that can provide real-time data and diagnostic information. In different examples, the OBD connector may be one of a variety of types, such as a multiplex OBD, an OBDI, an OBD1.5, an OBDII, or a future type of wired or wireless OBD connector. Each of these different types of OBD connectors comply with specific industry standards, such as those set by the Society of Automotive Engineers (SAE).

In one more detailed example, the OBD connector is an OBDII connector, which complies with SAE standards J1962, which itself a subset of International Standards Organization (ISO) standard 15031-1. The OBDII standard port and communications system are present on all cars sold in the United States since 1996, and so are present on the vast majority of vehicles currently in use. Among the specifications detailed in the standards is a requirement that the OBDII connector 102 be located within easy reach of the driver's seat, such as within an area of the dashboard bounded by the driver's end of the dashboard to 300 mm beyond the vehicle centerline on the dashboard, with a preferred location between the steering column and vehicle centerline. The specification also indicates that the OBDII connector should be easy for a person to access from the driver's seat location, and mounted in such a way to facilitate easy mating and un-mating of an OBDII connector on a diagnostic tool or other such connected device.

The OBDII connector therefore provides an easy and convenient interface to the car's electrical system from the driver's seat location in most vehicles implementing these standards, which have been in effect starting with 1996 model year vehicles. Various examples discussed herein will therefore use the vehicle's OBDII port to access various systems within the vehicle, such as to control systems such as the fuel pump or starter, or to monitor systems such as the speed or mileage of the vehicle. Other versions of OBD connectors will be used in other example embodiments.

Figure 2A:
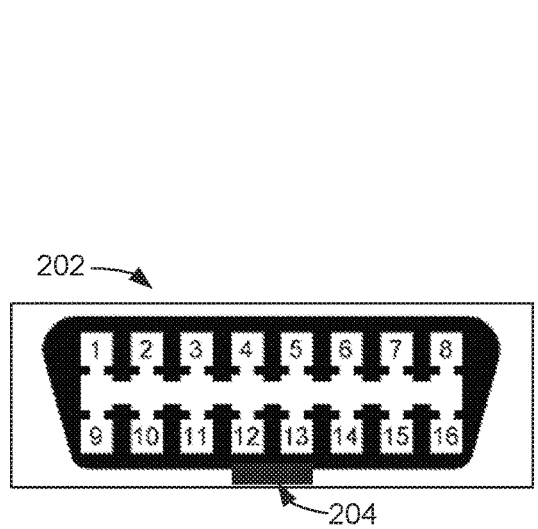
FIG. 2A shows a detailed example of an On-Board Diagnostic (OBDII) connector.

FIG. 2A shows a detailed example of an On-Board Diagnostic (OBDII) connector. Here, a connector 202 has 16 pins or discrete electrical contacts numbered consistent with the standards discussed above. Although some pins are unused, each of the pins used in a particular connection provides access to a data bus within the vehicle, or provides power or a ground signal for a device connected to the car. The connector mounted to the car as shown in FIG. 1 is a female connector having a socket designed to receive a pin at each location numbered in FIG. 2, while devices designed to plug in to the connector on the car are male connectors having pins at each numbered location. The OBDII connectors are designed such that a male connector can be easily attached to a female connector by aligning the plastic connector housings and pushing the connectors together, and can be removed by firmly pulling the connectors apart. The OBD connectors are held together when assembled in some examples through use of a retention element 204 on the female OBDII connector, which is engaged by a spring biased member on the male OBDII connector. This makes attachment and removal of various devices using OBDII connectors very straightforward, requiring little time or effort and no advance training or tools.

Figure 2B:
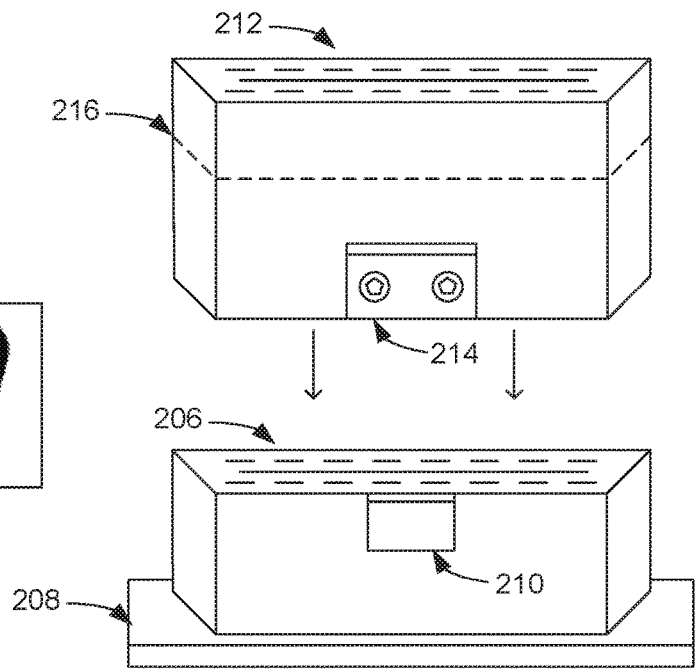
FIG. 2B shows a vehicle-mounted OBDII connector and a pluggable OBDII module.

FIG. 2B shows a vehicle-mounted OBDII connector and a pluggable OBDII module. Here, the OBDII connector 206 is mounted to a vehicle, as shown at 102 of FIG. 1. The OBDII connector is a female connector, and is mounted to the vehicle using mounting flange 208. The OBDII connector 206 also includes a standard retention element 210, which is operable to engage a spring-biased retention element on a male plug to ensure that the male plug doesn't easily become dislodged from the female connector mounted to the vehicle. Typically, the spring-biased retention element on the male plug results in a force of several pounds being needed to separate the male plug from the female OBDII connector 206.

An OBDII dongle 212 is also shown in FIG. 2B, which includes a locking retention element 214. The OBDII dongle in this example is configured to plug into the OBDII connector 206 and to lock in place using secure screws that are part of locking retention element 214, which selectively engages the OBDII connector 206's retention element 210 after the OBDII dongle 212 is plugged into OBDII connector 206 up to approximately line 216. Because the locking retention element 214 is not spring-biased but instead locks in place using secure screws or other such methods, the OBDII dongle 212 will be difficult to remove or tamper with except by approved installers having proper tools and training. This reduces the likelihood that the OBDII dongle 212 is removed by the user, such as an intoxicated vehicle owner trying to start a vehicle by tampering with elements of an intoxication interlock system. The locking retention element 214 in this example supplements the spring-biased retention element of at least part of the OBDII connection, but in other examples a locking retention element such as 214 will engage or lock onto another part of the OBDII connector 206, such as locking onto flange 208.

The OBDII dongle 212 in this example further includes a pass-through connector, shown at the top in FIG. 2B. This enables connecting an intoxication interlock system to the car via the OBDII dongle 212, while also providing a replacement OBDII port that is also coupled to the car's OBDII port for diagnostics, data gathering, or other purposes. In an alternate example, the OBDII dongle 212 does not provide a replacement OBDII port. In one such example, the OBDII dongle 212 provides a "dummy" or non-functional OBDII connector that is not operational, but that is designed to appear as though it is a standard OBDII interface to reduce the possibility of a user tampering with the OBDII dongle 212.

In some examples, the OBDII dongle 212 provides an alternate wired or wireless interface. In another such example, the OBDII dongle 212 has a closed or sealed housing instead of a connection interface. In some embodiments, the OBDII dongle 212 derives power from the OBDII port, such as to power circuitry or communications elements within the OBDII dongle. In some embodiments, the OBDII dongle 212 communicates with one or more other elements of the intoxication interlock system through a wired connection, or through a wireless connection such as Bluetooth, NFC, WiFi, or another suitable wireless protocol. This enables the OBDII dongle to serve as an interface between the intoxication interlock system and the vehicle's control systems and networks, while providing some degree of physical security or tamper resistance through the locking retention element 214.

Figure 3:
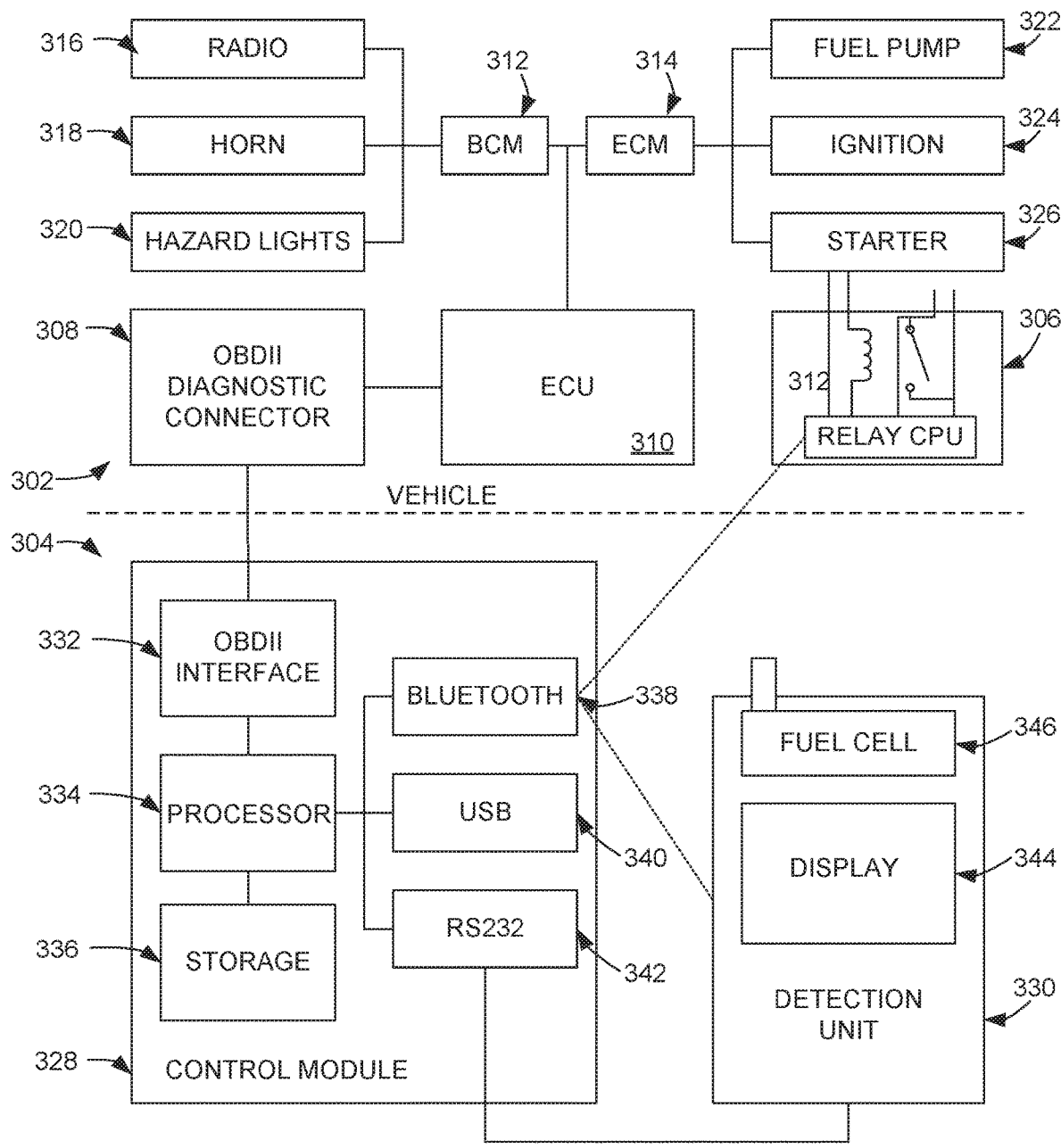
FIG. 3 shows an example intoxication interlock system coupled to a vehicle.

FIG. 3 shows an example intoxication interlock system coupled to a vehicle. Here, vehicle electrical systems 302 are connected to intoxication interlock system components 304. A Bluetooth relay 306 is also installed in the vehicle in place of a standard vehicle relay, as part of the intoxication interlock system.

The vehicle subsystem 302 comprises an OBDII diagnostic connector 308, which is connected to the vehicle's electronic control unit or ECU 310. The ECU is connected to various electrical subsystems within the vehicle using a bus such as a car area network bus or CANBUS, including body control module (BCM) 312 and engine control module (ECM) 314. The BCM is coupled to electrical systems that are a part of the car's body and that are not integral to operation of the engine or powertrain, such as the radio 316, the horn 318, and the hazard lights 320. The ECM is coupled to electrical systems that are associated with the vehicle's engine or powertrain, such as the fuel pump 322, the ignition 324, and the starter 326. In other examples, other modules such as a powertrain control module (PCM) or the like will control various elements shown as controlled by the ECM or BCM in this example.

The vehicle-connected intoxication interlock system 304 includes a control module 328 and a detection unit 330, which are coupled to the vehicle through the vehicle's OBDII diagnostic connector 308. In this example, the control module 328 includes an OBDII interface to communicate with the vehicle, a processor 334 to execute program instructions, and storage 336 to store program code used to implement various intoxication interlock functions. The control module also includes a wireless Bluetooth communications module 338, a Universal Serial Bus (USB) module 340, and an RS232 serial port 342. Although some examples include more, fewer, or different communication modules than those shown at 338-342, the communication modules illustrated here are representative of typical communication modules as may be used to implement various examples.

The detection unit 330 includes a display 344 operable to display text or graphics to a user, and a fuel cell 346 or other detection element operable to detect the presence and/or level of an intoxicant. In a more detailed example, a fuel cell operable to detect the level of ethanol in a user's breath is employed. The detection unit 330 is coupled to the control module through connection 348, which in this example is a RS232 serial connection, but in alternate embodiments is a Bluetooth wireless connection or other suitable connection. The detection unit in this example is a handheld device, such that a user may pick the unit up to facilitate conducting a breath test using the fuel cell 364.

To install the intoxication interlock system 304 in the vehicle of FIG. 2, the control module 328 is coupled to the vehicle's electrical system by connecting the OBDII interface 332 of the control module to the OBDII diagnostic connector 308 of the vehicle (also shown as OBDII diagnostic connector 102 of FIG. 1). This is achieved by simply connecting a cable extending from the control module to the vehicle's OBDII port in some embodiments. Other embodiments will use a wireless connection such as a Bluetooth transceiver coupled to the vehicle's OBDII diagnostic connector in communication with the Bluetooth module 338 of the control module. This step of connecting the control module 328 to the OBDII connector 308 does not require the use of any tools and can be performed with the installer's hands by pushing the cable extending form the control module into the vehicle's OBDII port 308, or by pushing the Bluetooth transceiver into the vehicle's OBDII port 308.

In a further example, the Bluetooth relay 306 is also installed in the vehicle, enabling the control module 328 to selectively allow operation of the Bluetooth relay 306. The Bluetooth relay 306 is installed by removing one of the standard vehicle relays and replacing it with the Bluetooth relay 306. In one example, this step does not require the use of any tools and can be performed with the installer's hands.

The installer identifies the appropriate standard relay for removal, pulls the standard relay out of the vehicle, which leaves an unoccupied relay receptacle, and the installer pushes the Bluetooth relay 306 into the relay receptacle of the vehicle. The Bluetooth relay in a further example closely resembles the standard relay thereby discouraging tampering, and the control module records vehicle events that may suggest the Bluetooth relay has been removed or replaced.

Installation of the intoxication interlock system of FIG. 3 is therefore significantly less difficult than installing a traditional intoxication interlock system in a vehicle, which typically requires several hours of cutting holes in the firewall, cutting and splicing wires, and routing wiring from the control module to various electrical systems within the vehicle. The intoxication interlock system of FIG. 3 instead uses a networked configuration, including use of a vehicle network such as an OBDII network to communicate with a vehicle's control systems, and use of a Bluetooth network to communicate with a replacement relay. This networked configuration makes use of wireless and wired networks including existing vehicle networks, thereby reducing reduces the cost of installation of an intoxication interlock system and reducing damage to the vehicle into which such a system is installed.

In operation, the control module 328 derives power through the OBDII diagnostic connector, through batteries, or though both to power a processor 334 and other circuitry to perform basic intoxication interlock functions. The control module is connected to a detection unit 330 that is operable to perform functions such as display a current status or provide instructions to a user using display 344, and to receive a breath sample for analysis using fuel cell 346 or another such detection element. The detection unit and control module are shown as separate elements in the example of FIG. 3, but in other examples can be integrated into the same physical unit, can be implemented in whole or in part using other devices such as a user's smartphone, and may include fewer or additional features from the example shown here.

To start a vehicle, a user typically turns the vehicle key to the run position to power the vehicle systems and to power the control module through the vehicle's OBDII diagnostic connector. When the control module receives the power signal from the vehicle, it initiates communication with the vehicle and starts an intoxication interlock procedure. The procedure in one example includes prompting a user via the display 344 to blow a breath into fuel cell 346 that is sufficiently long and has a sufficient volume of air to verify that the user is not intoxicated, such as having an ethanol level in breath that is lower than a preset threshold. If the user's breath passes the intoxication test, the control module signals the vehicle to enable the vehicle to start, such as by enabling one or more vehicle systems that have been previously disabled via the OBDII diagnostic connector, writing or modifying at least a portion of previously altered firmware of a control system within the vehicle to enable the vehicle to start, or signaling Bluetooth relay 306 to enable the relay to operate normally.

If the user's breath does not pass the test, the control module selectively restricts operation of the vehicle. In one example, the control module does not allow the vehicle to start, and records a violation or a failed test. The control module prevents the vehicle from starting in one example by leaving the Bluetooth relay 306 in a deactivated mode or putting the Bluetooth relay 306 into a deactivated mode such that it does not function as a normal relay. In another example, the control module prevents the vehicle from starting by writing or leaving a portion of firmware of one of the vehicle's control systems modified such that the vehicle is inoperable. In another example, the control module prevents the vehicle from starting by disabling a vehicle system such as the fuel pump, ignition, starter, etc. via the OBDII diagnostic connector.

Once the vehicle is in operation, the control module will occasionally and randomly prompt a retest. A retest requires the driver to provide another breath sample to the detection unit 330. Although official documentation suggests that the retest be conducted after the driver has pulled off the road and stopped the vehicle, the Federal Register recognizes that 99% of retests are done while the vehicle remains in normal operation. When the driver is prompted to perform a retest, the driver typically must perform the retest within a relatively short time, such as a minute or several minutes, or the control module 328 may take various actions to encourage the driver to complete the retest or restrict operation of the motor vehicle.

In one such example, the control module 328 responds to a failed retest or a retest not completed in a timely manner by providing an indication that the retest has not been successfully completed, such as by honking the horn 318 or flashing the hazard lights 320. In a further example, the radio 316 is turned down to a minimal volume level or is turned off to make audible prompts to complete a retest more easily recognized. In another example, the controller responds to failure to complete a retest by restricting vehicle operation, such as by gradually reducing vehicle speed to a governed speed that enables the driver to safely control and stop the vehicle.

Figure 4:
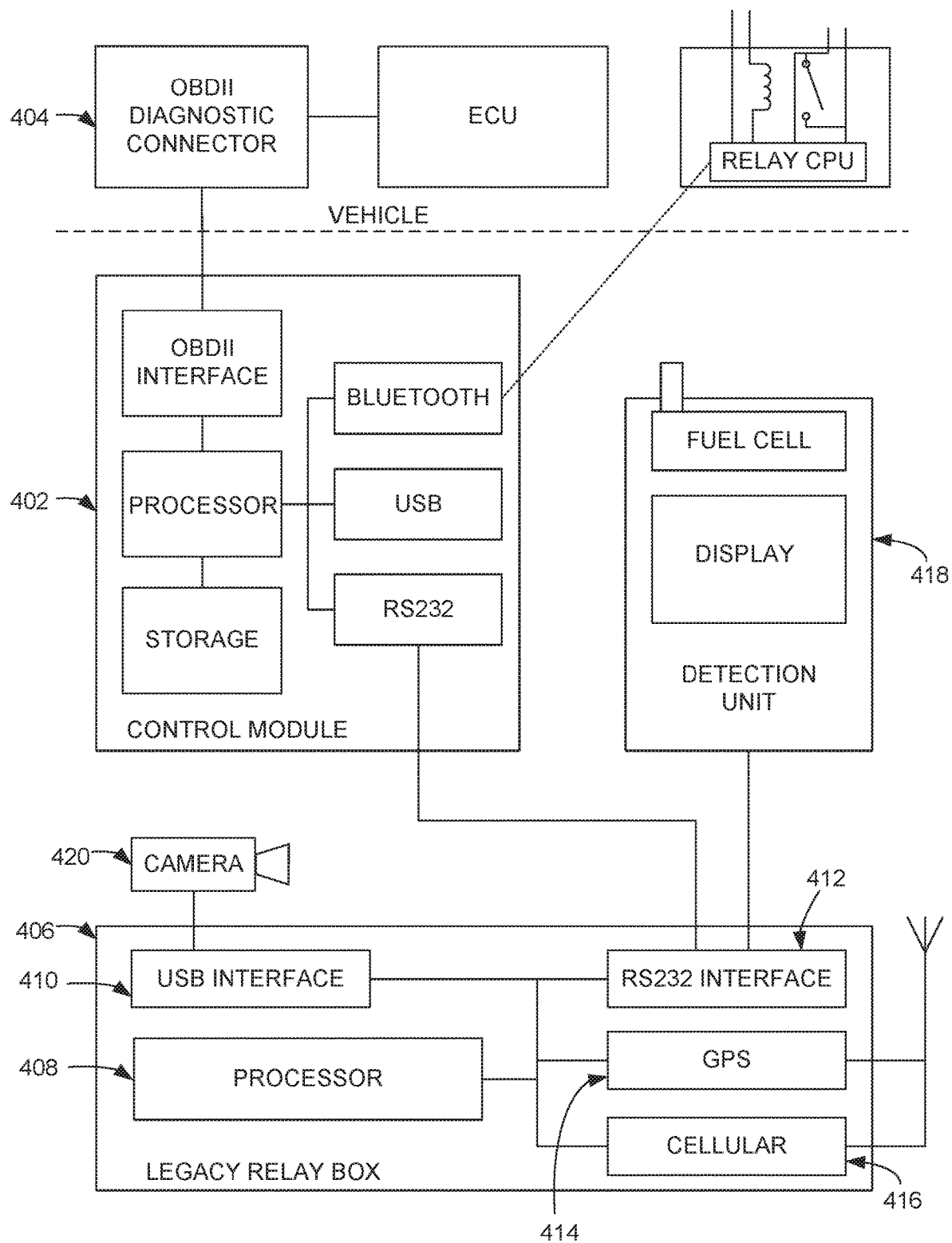
FIG. 4 shows an intoxication interlock system incorporating a legacy relay box, consistent with an example.

The intoxication interlock system of FIG. 3 shows a system in which a control module 328 and a detection unit 330 that are either separate items or are combined into a single unit may be structured. Other examples will use other configurations, such as incorporation of additional or legacy functions from preexisting intoxication interlock systems which are designed to be installed by the preexisting methods of cutting holes in the firewall, cutting and splicing wires, and routing wiring from the control module to various electrical systems within the vehicle. FIG. 4 shows an intoxication interlock system incorporating a legacy relay box, consistent with one such example.

Here, a control module 402 such as the control module of FIG. 3 is coupled to the vehicle's OBDII diagnostic port 404, such as via a cable assembly or a wireless connection. The control module 402 is also coupled to a legacy relay box 406, which incorporates its own processor 408, USB interface 410, RS232 serial interface 412, Global Positioning System or GPS 414, and cellular modem 416. The legacy relay box 406 is coupled to the control module 402, providing the control module access to a variety of external functions such as a camera 420, GPS location information, cellular radio communication capability, and connection to a detection unit 418. These additional functions are already implemented in the legacy relay box 406, and may be used in some embodiments to provide the intoxication interlock system with additional levels of security or verification.

For example, a USB port 410 and camera 420 enable the intoxication interlock system to record pictures or video of the person breathing into the fuel cell to complete the breath test, to document if a person other than the driver is blowing into the fuel cell. This significantly reduces the ability of a user who is required to use the intoxication interlock system to falsely appear to pass the test by having someone else complete the breath test, adding to the safety and security of the intoxication interlock system. Similarly, a GPS receiver 414 is operable to track the location of the legacy relay box 406, and therefore of the vehicle, enabling the control module to record the location of various tests, and to perform other functions such as to detect if the vehicle is moving when a valid intoxication breath test has not been completed.

The control module 402 in the example of FIG. 4 is also able to use the cellular modem 416 to communicate with remote systems, such as to report movement of the vehicle, to report violations or attempts to defeat the intoxication interlock system, or to send test information such as photos accompanying each intoxication test to a monitoring agency to ensure that only the intended user is completing the breath intoxication tests. In the example shown here, the GPS 414 and cellular modem 416 are also coupled to one or more antennas, which may be integrated into the legacy relay box or in other examples may be external to the relay box.

The Bluetooth relay in the examples of FIGS. 3 and 4 is in various embodiments operable to replace a relay in a vehicle by simply unplugging the original relay and inserting the Bluetooth relay in its place. In some examples, the Bluetooth relay is configured to have an appearance similar to the original relay such that a user is not tempted to remove or tinker with the relay, while in other examples the Bluetooth relay will be identifiable as part of the intoxication interlock system, such as with a warning not to remove the relay. In a further example, the control module is operable to detect and record abnormal operation of the vehicle or Bluetooth relay, which may suggest that the Bluetooth relay has been removed, replaced, or tampered with.

Although the Bluetooth relay of FIGS. 3 and 4 is wireless and the control module connection to the vehicle's OBDII diagnostic connector is wired, either of these connections may be wired or wireless in various embodiments. For example, a wire coupling the control module to the relay may be less convenient than a Bluetooth or other wireless connection, but is still significantly more convenient than cutting and splicing wires on a customer's vehicle. Similarly, added convenience may be obtained by using a wireless transceiver dongle or connector coupled to the OBDII diagnostic connector of the vehicle, which wirelessly communicates with the control module. In an alternate example, the connection between the control module and the detection unit is wireless, such that the control module may be hidden under the dash or otherwise concealed. This may help prevent tampering in installations where only the detection unit is exposed in the vehicle for customer interaction. In some such examples, the detection unit may be battery powered, powered using a cigarette lighter or USB port, or integrated into another powered device such as a smartphone.

Figure 5A:
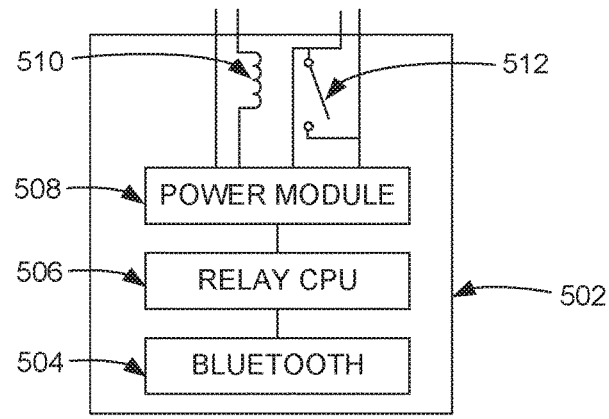
FIG. 5A shows a detailed example of a Bluetooth relay.

FIG. 5A shows an example of a more detailed Bluetooth relay. Here, the Bluetooth relay 502 includes a Bluetooth radio transceiver 504, a controller or central processing unit (CPU) 506, and a power module 508. The term "Bluetooth" is used herein to indicate that a component is capable of communicating according to a standard for wireless exchange of data over short distances, such as by using short-wavelength UHF radio waves in the ISM band from 2.4-2.485 Gigahertz. Standards for Bluetooth communication are managed by the Bluetooth Special Interest Group. The relay CPU and power module are connected to traditional relay elements including a relay actuation coil 510 and a switch 512 that is controlled by the relay actuation coil. In operation, the power module 508 derives power for the relay's CPU and Bluetooth elements from external pin connections to the relay actuation coil and the switch, such as by drawing power from a control signal applied across the relay actuation coil when the coil is energized, or drawing power from across the switch when the switch is open. Because the Bluetooth relay requires very little power to operate the CPU 506 and the Bluetooth transceiver 504, the amount of power drawn does not interfere with control signals provided to the relay's actuation coil or with a switched element connected to the relay's switch.

This enables the Bluetooth relay 502 to communicate with external devices such as the control modules of FIGS. 3 and 4 using Bluetooth radio communication, and to selectively control whether a control signal received in the relay actuation coil 510 will result in actuating the switch 512. This is done in some embodiments by selectively breaking the external pin connections to the coil 510, such as with a transistor or other device controlled by the relay CPU 506. The Bluetooth relay's controller can therefore activate or deactivate the Bluetooth relay in response to receive Bluetooth signals, making operation of the Bluetooth relay selectively controllable from a device such as the control module of FIGS. 3 and 4. Although the relay is used in the examples presented here to restrict operation of the vehicle under the control of the control module to enforce an intoxication interlock function, the relay shown can be employed in further examples as part of a car security system to prevent auto theft, or as part of a seller payment assurance system operable to permit a seller to remotely disable the vehicle if the user does not make payments for the vehicle in other examples.

Figure 5B:
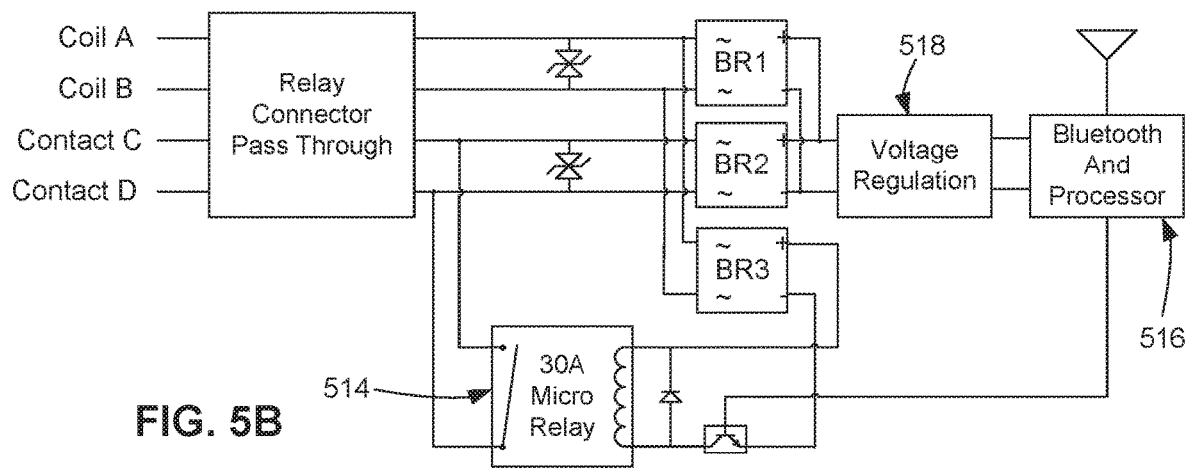
FIG. 5B shows another detailed example of a Bluetooth relay.

FIG. 5B shows a more detailed example of a Bluetooth relay. Here, the relay actuation coil is coupled between coil contacts A and B, and the switch is coupled between contacts C and D. An actual physical micro relay 514 is incorporated into the Bluetooth relay 502 and includes the actuation coil and switch. Bridge rectifiers BR1 and BR2 serve to derive power from the coil connections A and B when the coil is energized, and from switch contacts C and D when the switch is open. Bridge rectifier BR3 energizes the coil of micro relay 514 in response to receiving an energizing signal on coil connections A and B, under the control of microcontroller and Bluetooth receiver 516.

The microcontroller and Bluetooth receiver shown at 516 are powered by the output from bridge rectifiers BR1 and BR2, using a power signal regulated by voltage regulator 518. The power is derived via both bridge rectifiers BR1 and BR2 in this example so that when the normally-open relay is not energized, power can be derived from across the open contact connections C and D coupled to the switch. When the relay is energized, the voltage across the now-closed switch will be near zero, and power will instead be derived from across the coil contacts A and B. The rectifiers further allow installation of the relay in relay sockets using different pin configurations, as power applied to any of the pins can be used to power the relay.

Figure 5C:
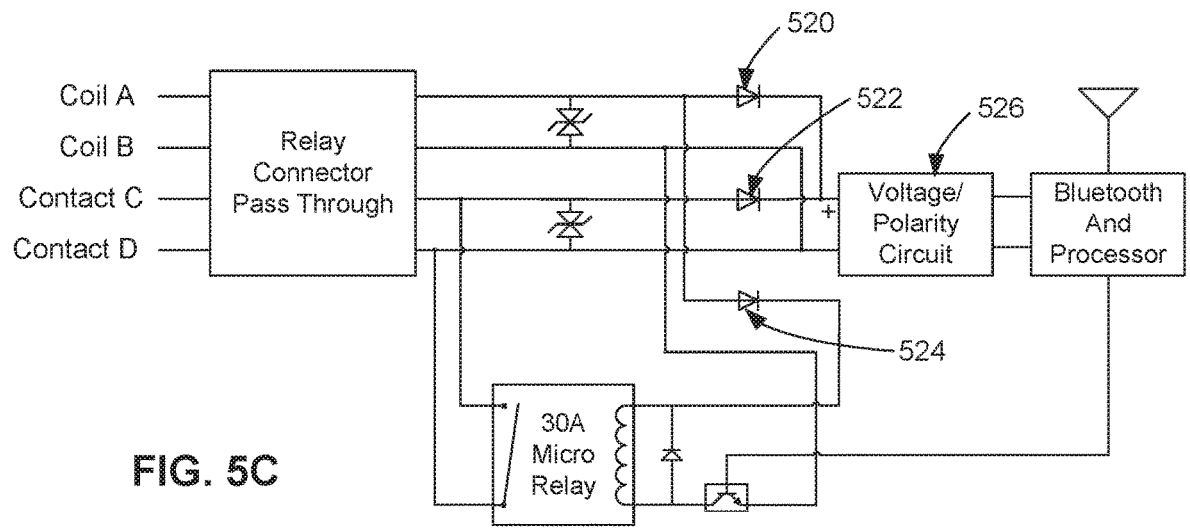
FIG. 5C shows an alternate detailed example of a Bluetooth relay.

FIG. 5C illustrates an alternate embodiment of a Bluetooth relay, in which diodes are used in place of bridge rectifiers. Here, diodes 520, 522, and 524 can be employed as polarity protection in place of rectifiers because the polarity of signals applied to the relay contacts when correctly installed is known, and the diodes are only used to protect against damage from installation in a reversed physical configuration or in an incompatible vehicle. In another example, the relay will use means other than a bridge rectifier or diodes to manage unknown contact polarity, such as a transistorized circuit that switches the contact signal applied to the voltage regulation circuit 518 dependent on the relative voltage detected between two or more of the contacts.

In a further example, voltage regulation and polarity detection circuit 526 is operable to indicate when the relay is properly plugged in and powered, such as by illuminating or flashing a light-emitting diode (LED) for a brief period of time to indicate to an installer that the relay is correctly installed and powered. An installer who does not see the LED flash can therefore easily see that the relay is not installed correctly, and can reconfigure the relay in the relay socket or try another relay as needed. Because it is desirable in some applications not to draw attention to the relay once installed for security purposes, in one example the indicator LED or other indication such as a buzzer will only alert for a brief period during the installation process, and then will be turned off during normal operation. The LED or other indication may also be obscured in some examples to further disguise its presence, such as by shielding it behind a semi-opaque or semi-transparent cover. The relays shown in FIG. 5 incorporate electrically-controlled electromagnetic switching elements, but the relay in other examples includes solid-state relays or other suitable devices. The term "relay" as used herein includes any electrically-controlled switching devices or circuits operable to selectively change the state of the switching device or circuit using an electrical control signal.

The relays of FIGS. 5A, 5B, and 5C are in some embodiments operable to both receive and send information, such as to receive signals indicating an active or inactive state for the relay, and to report their presence or state to another device such as a control module. In a more detailed example, the Bluetooth relay is in a disabled state when initially powered on, such as by a user turning an ignition key on. The relay establishes communication with the control module, thereby confirming its presence to the control module, and awaits a signal to enable the relay function. When the control module has determined that the user is not intoxicated, it signals the Bluetooth relay to enable itself, making the car operable.

The control module can further send a code to the relay causing the relay to disable normal relay operation, such as when a user fails a retest while driving by providing a breath having an alcohol level that exceeds an acceptable threshold. In such circumstances, the Bluetooth relay receives a disable code from the control module and disables the vehicle, which in a further example may occur after some brief period of the control module enforcing limited operation such as reduced speed or fuel delivery that enables the driver to safely pull the vehicle out of traffic. In a further example, the control module will activate the vehicle's hazard lights, horn, or other indicators to warn other drivers that the vehicle is being stopped as a result of an intoxicated driver.

The control module of FIGS. 3 and 4 is presented as a microprocessor operable to perform various functions, with various communication capabilities to connect with the vehicle, with a cellular monitoring system, with a camera, and the like. In some embodiments, the control module will be embodied in part or in whole by a smartphone or other portable handheld device. The term smartphone is used to indicate a mobile phone with an advanced mobile operating system so that some functionalities of a personal computer are provided.

Figure 6:
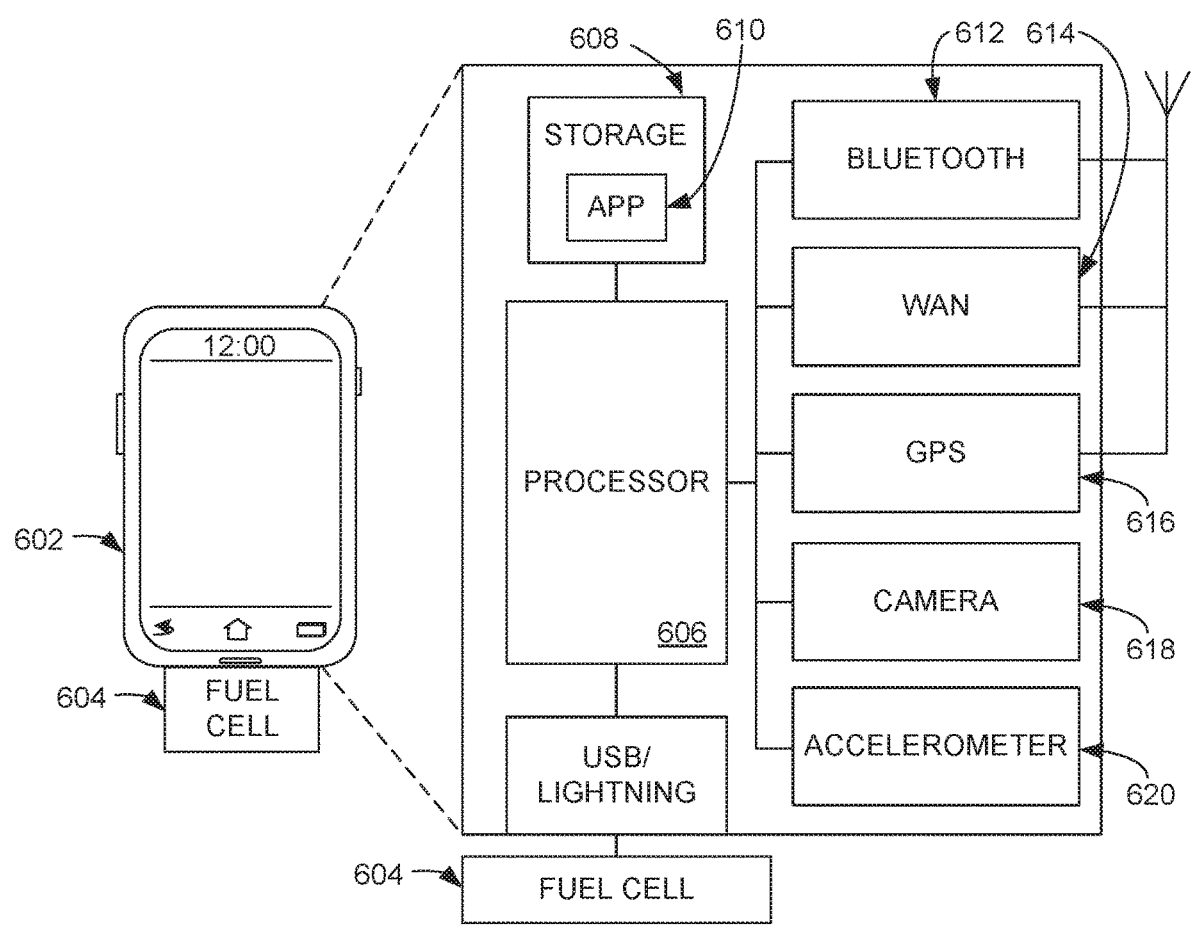
FIG. 6 shows a smartphone configured to function as a control module for an intoxication interlock system, consistent with an example.

FIG. 6 shows a smartphone configured to function as a control module for an intoxication interlock system, consistent with an example. Here, the smartphone 602 is coupled to a fuel cell 604 or other device operable to detect intoxication in a user's breath, such as by connecting to the smartphone's USB port, charging port, Lightning connector available from Apple Inc. for Apple mobile devices, or other suitable connection. The smartphone comprises a processor 606, and storage 608 which stores application software 610, referred to hereinafter as an app 610, that is operable to perform at least some functions of the intoxication interlock system. The app 610 is able to take advantage of other features common to a smartphone, such as the phone's Bluetooth radio 612, cellular radio or wide-area network (WAN) 614, global positioning system or GPS 616, camera 618, and accelerometer 620.

As with the examples of FIGS. 3 and 4, the Bluetooth radio 612 can be used to communicate with a Bluetooth relay, with a OBDII wireless interface such as the OBDII dongle 212 of FIG. 2B, or with other components of the intoxication interlock system. The cellular or WAN connection 614 may again be used to communicate information from the controller to a remote monitor or remote server, such as to transmit violation records or images of users while taking intoxication tests to verify identity. Similarly the GPS 616 may be used to verify or track the location of the vehicle, and may further be used in conjunction with or as an option to accelerometer 620 to ensure that the vehicle is not moving until a valid intoxication interlock test has been completed. Camera 618 can capture images of the person taking an intoxication test, such that the images are recorded or are transmitted such as via the cellular radio to monitor that the correct person is taking the intoxication tests.

Although the intoxication interlock systems of FIGS. 3, 4, and 6 have addressed restricting operation of a vehicle when a user is intoxicated, the intoxication interlock system in further examples is operable to perform one or more additional functions, such as detecting impairment or intoxication as a result of a substance other than alcohol. In other such examples, the system is operable to function as an automotive security system operable to prevent theft of the vehicle, or as a seller payment assurance system operable to permit a seller to remotely disable the vehicle if the user does not make payments for the vehicle. In another example, the system is operable to detect when someone is sending a text message while driving, or performing another restricted action using electronics within the car. The system in other examples will be able to limit the geographic range in which the driver can operate the vehicle, such as permitting a user to drive only to work and back or within the driver's neighborhood. In another example, the system will function to restrict other vehicle operation parameters such as speed or time-of-day of vehicle operation.

Figure 7:
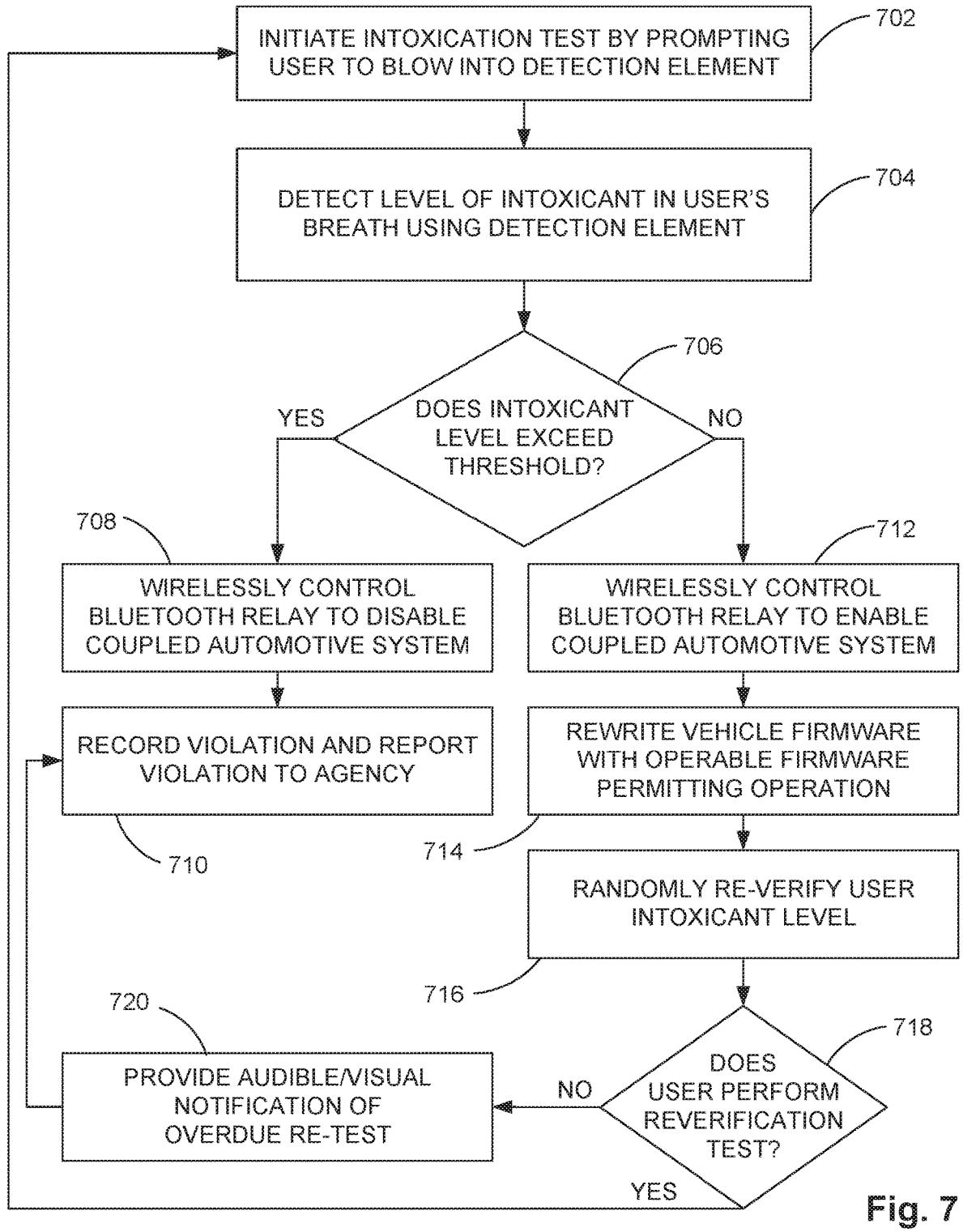
FIG. 7 is a flowchart illustrating an example method of operating an intoxication interlock system.

FIG. 7 is a flowchart illustrating an example method of operating an intoxication interlock system. At the start, the vehicle is in a disabled or inactive state. The process of enabling the vehicle starts by the intoxication interlock system prompting the user to blow into the intoxication interlock system's detection element at 702, and the detection element detects the level of an intoxicant such as alcohol in the user's breath at 704. The system then compares the detected intoxicant level to an allowable threshold at 706, and determines whether the intoxicant level exceeds the threshold.

If the threshold is exceeded at 706, the vehicle is brought to a disabled state if it is not already disabled at 708, such as by wirelessly controlling a Bluetooth relay to bring an automotive system coupled to the relay to an inoperative state. By making an automotive system such as the starter, the fuel pump, or the ignition inoperable, the vehicle will not start or run. In another example, the intoxication interlock system interrupts a vehicle bus such as the On-Board Diagnostic (OBDII) bus, car-area network bus (CANBUS), or other vehicle bus by disrupting the bus to prevent operation of the vehicle. In one such example, the intoxication interlock system shorts the data bus through its connection to the vehicle's OBDII diagnostic connector, thereby preventing communication on the bus. In another example, the intoxication interlock system injects noise or other signals onto the bus that prevent normal operation of the bus. The intoxication violation is then recorded at 710, such as by storing a record of the violation in the intoxication interlock system or reporting the violation to a monitoring agency or authority.

A vehicle bus such as the OBDII bus or CANBUS is used to restrict operation of the vehicle in another example by sending instructions from the intoxication interlock system to one or more car components, such as the fuel pump, starter relay, or ignition. By selectively instructing one or more vehicle systems or components such as these not to operate, the intoxication interlock system is able to selectively restrict operation of the vehicle. In a further example, the intoxication interlock system instructs one or more systems to operate to selectively prevent operation of the vehicle, such as activating a parking brake, vehicle security system, or other component that can restrict operation of the vehicle.

If the threshold is not exceeded at 706, the intoxication interlock system wirelessly controls the Bluetooth relay to enable the coupled automotive system at 712. In alternate or further embodiments, the intoxication interlock system rewrites at least a portion of vehicle firmware at 714 that has been previously modified to make the firmware operable to control normal vehicle operation, or performs another function enabling some element of the vehicle.

Once normal operation of the vehicle has been enabled as a result of successful completion of an intoxication interlock test, the intoxication interlock system randomly re-tests or re-verifies the user's sobriety at 716. This safeguards against using a sober friend to pass a test before an intoxicated user begins driving, except where the sober friend is also a passenger in the vehicle. If the user performs the re-verification test at 718, the intoxication interlock process is repeated at 702, except that the current state of the vehicle when the test starts will be an enabled or operable state. If the user does not perform the re-verification test at 718 when prompted, the intoxication interlock system provides an audible and/or visible notification that the re-verification test is overdue at 720, such as by honking the vehicle's horn and turning down the radio, or flashing the hazard lights of the vehicle. If the re-verification test is still not performed in a timely manner, failure to complete the re-verification test is recorded as a violation at 710, and in a further example is reported to a monitoring agency or authority.

These examples show how an intoxication interlock system incorporating features such as a Bluetooth relay or an OBDII diagnostic port interface may operate to selectively restrict operation of a vehicle, depending on the result of an intoxication test. The systems and methods presented here may be implemented in part using a computerized device, such as a smartphone, handheld, or other computerized device.

Figure 8:
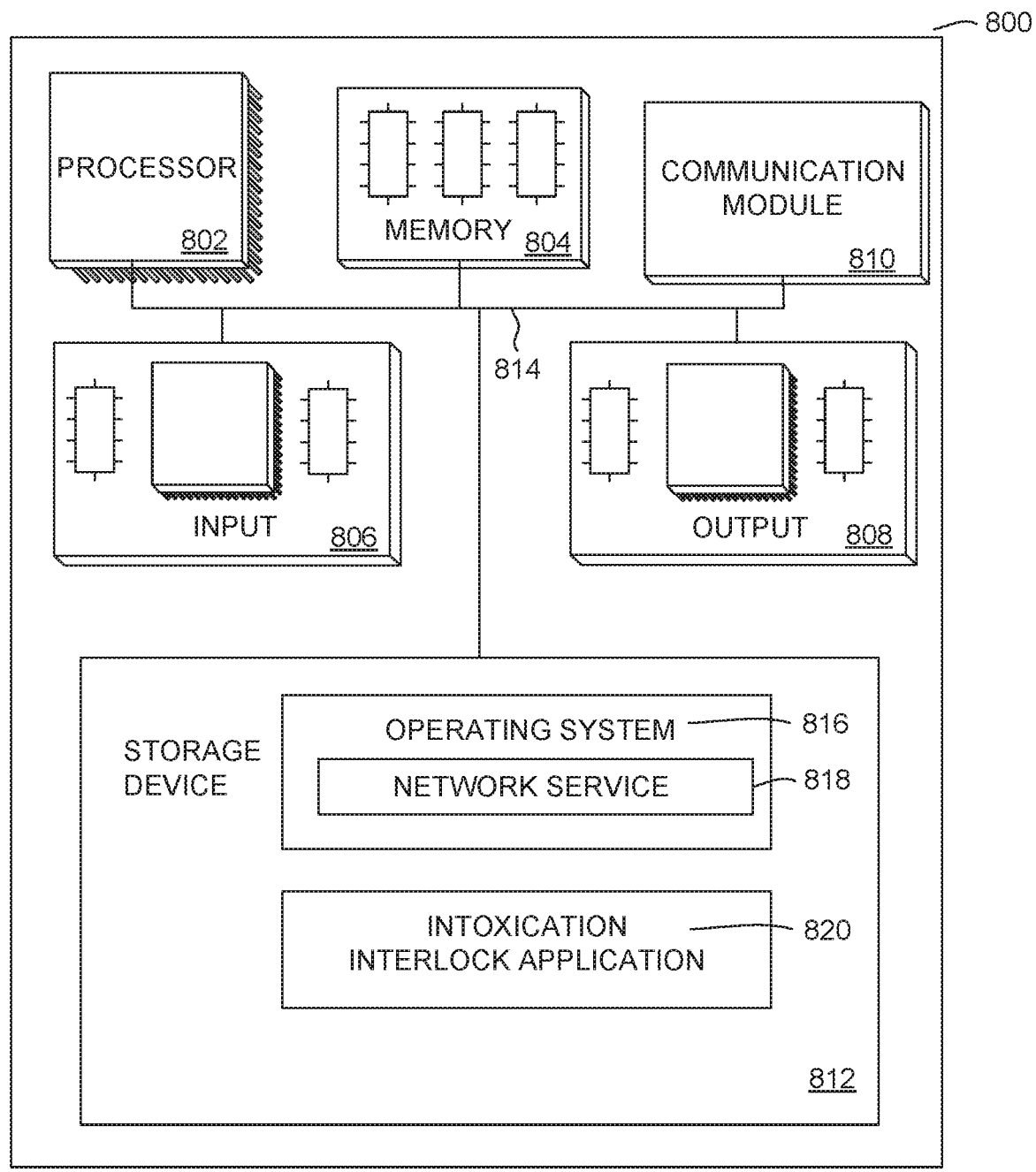
FIG. 8 shows a computerized intoxication interlock system, as may be used to practice various examples described herein.

FIG. 8 shows a computerized intoxication interlock system or component of a computerized intoxication interlock system, consistent with various examples described herein. FIG. 8 illustrates only one particular example of computing device 800, and other computing devices 800 may be used in other embodiments. Although computing device 800 is shown as a standalone computing device, computing device 800 may be any component or system that includes one or more processors or another suitable computing environment for executing software instructions in other examples, and need not include all of the elements shown here. A control module, relay box and detection unit as described herein are examples of components that can be implemented using computing devices such as computing device 800.

As shown in the specific example of FIG. 8, computing device 800 includes one or more processors 802, memory 804, one or more input devices 806, one or more output devices 808, one or more communication modules 810, and one or more storage devices 812. Computing device 800, in one example, further includes an operating system 816 executable by computing device 800. The operating system includes in various examples services such as a network service 818. One or more applications, such as an intoxication interlock application 820 are also stored on storage device 812, and are executable by computing device 800.

Each of components 802, 804, 806, 808, 810, and 812 may be interconnected (physically, communicatively, and/or operatively) for inter-component communications, such as via one or more communications channels 814. In some examples, communication channels 814 include a system bus, network connection, inter-processor communication network, or any other channel for communicating data. Applications such as intoxication interlock application 820 and operating system 816 may also communicate information with one another as well as with other components in computing device 800.

Processors 802, in one example, are configured to implement functionality and/or process instructions for execution within computing device 800. For example, processors 802 may be capable of processing instructions stored in storage device 812 or memory 804. Examples of processors 802 include any one or more of a microprocessor, a controller, a digital signal processor (DSP), an application specific integrated circuit (ASIC), a field-programmable gate array (FPGA), or similar discrete or integrated logic circuitry.

One or more storage devices 812 may be configured to store information within computing device 800 during operation. Storage device 812, in some examples, is known as a computer-readable storage medium. In some examples, storage device 812 comprises temporary memory, meaning that a primary purpose of storage device 812 is not long-term storage. Storage device 812 in some examples includes a volatile memory, meaning that storage device 812 does not maintain stored contents when computing device 800 is turned off. In other examples, data is loaded from storage device 812 into memory 804 during operation. Examples of volatile memories include random access memories (RAM), dynamic random access memories (DRAM), static random access memories (SRAM), and other forms of volatile memories known in the art. In some examples, storage device 812 is used to store program instructions for execution by processors 802. Storage device 812 and memory 804, in various examples, are used by software or applications running on computing device 800 such as intoxication interlock application 820 to temporarily store information during program execution.

Storage device 812, in some examples, includes one or more computer-readable storage media that may be configured to store larger amounts of information than volatile memory. Storage device 812 may further be configured for long-term storage of information. In some examples, storage devices 812 include non-volatile storage elements. Examples of such non-volatile storage elements include magnetic hard discs, optical discs, floppy discs, flash memories, or forms of electrically programmable memories (EPROM) or electrically erasable and programmable (EEPROM) memories.

Computing device 800, in some examples, also includes one or more communication modules 810. Computing device 800 in one example uses communication module 810 to communicate with external devices via one or more networks, such as one or more wireless networks. Communication module 810 may be a network interface card, such as an Ethernet card, an optical transceiver, a radio frequency transceiver, or any other type of device that can send and/or receive information. Other examples of such network interfaces include Bluetooth, 3G or 4G, WiFi radios, and Near-Field Communications (NFC), and Universal Serial Bus (USB). In some examples, computing device 800 uses communication module 810 to wirelessly communicate with an external device such as via public network such as the Internet.

Computing device 800 also includes in one example one or more input devices 806. Input device 806, in some examples, is configured to receive input from a user through tactile, audio, or video input. Examples of input device 806 include a touchscreen display, a mouse, a keyboard, a voice responsive system, video camera, microphone or any other type of device for detecting input from a user.

One or more output devices 808 may also be included in computing device 800. Output device 808, in some examples, is configured to provide output to a user using tactile, audio, or video stimuli. Output device 808, in one example, includes a display, a sound card, a video graphics adapter card, or any other type of device for converting a signal into an appropriate form understandable to humans or machines. Additional examples of output device 808 include a speaker, a light-emitting diode (LED) display, a liquid crystal display (LCD), or any other type of device that can generate output to a user.

Computing device 800 may include operating system 816. Operating system 816, in some examples, controls the operation of components of computing device 800, and provides an interface from various applications such intoxication interlock application 820 to components of computing device 800. For example, operating system 816, in one example, facilitates the communication of various applications such as intoxication interlock application 820 with processors 802, communication unit 810, storage device 812, input device 806, and output device 808. Applications such as intoxication interlock application 820 may include program instructions and/or data that are executable by computing device 800. As one example, intoxication interlock application 820 may include instructions that cause computing device 800 to perform one or more of the operations and actions described in the examples presented herein.

Although specific embodiments have been illustrated and described herein, any arrangement that achieve the same purpose, structure, or function may be substituted for the specific embodiments shown. This application is intended to cover any adaptations or variations of the example embodiments of the invention described herein. These and other embodiments are within the scope of the following claims and their equivalents.

The invention claimed is:

1. A vehicle immobilization system, comprising:
   a detection unit comprising:
      a detection unit housing configured to be picked up and hand held by a user, a fuel cell within the detection unit housing, wherein the fuel cell is operable to detect a presence of and a level of ethanol in a breath of the user, a display operable to display text to the user, a processor of the detection unit within the detection unit housing, the processor coupled to the display, and a memory of the detection unit within the detection unit housing, the memory coupled to the processor of the detection unit, wherein the detection unit is operable to send, via a serial connection, a signal related to the level of ethanol in the breath of the user;

a control module operable to receive the signal related to the level of ethanol in the breath of the user from the detection unit and to selectively restrict operation of a vehicle by restricting operation of a starter of the vehicle based on the level of ethanol in the breath of the user exceeding a threshold, the control module comprising:

a processor of the control module operable to:
receive the signal related to the level of ethanol in the breath of the user from the detection unit,
based on the signal, selectively restrict the operation of the vehicle by restricting the operation of the starter of the vehicle based on the level of ethanol in the breath of the user exceeding the threshold; and
based on the signal, selectively allow the operation of the vehicle by allowing the operation of the starter of the vehicle based on the level of ethanol in the breath of the user not exceeding the threshold;

a memory of the control module connected to the processor of the control module and storing instructions for the processor of the control module to selectively restrict the operation of the vehicle by restricting the operation of the starter of the vehicle based on the level of ethanol in the breath of the user exceeding the threshold and selectively allow the operation of the vehicle by allowing the operation of the starter of the vehicle based on the level of ethanol in the breath of the user not exceeding the threshold;

wherein the control module is configured to be hidden under a dashboard in the vehicle and the detection unit is configured to be exposed for user interaction;

wherein the control module is physically separate from the detection unit housing and is connected to the detection unit via the serial connection;

a communication module physically separate from and external to the control module, the communication module comprising:

a global positioning system (GPS) receiver, a cellular modem configured to send an intoxication test result associated with the level of ethanol in the breath of the user, a processor of the communication module connected to the GPS receiver and the cellular modem, and a memory of the communication module connected to the processor of the communication module, wherein the communication module is coupled to the control module via a serial connection;

wherein the GPS receiver and the cellular modem are coupled to a plurality of antennas integrated into the communication module; and a camera external to the control module, the communication module, and the detection unit, the camera configured to connect to a USB interface, the camera comprising a cable connection to the vehicle immobilization system, wherein the camera is configured to record a picture of the user using the detection unit.

2. The system of claim 1, wherein the control module is configured to record a violation if the breath of the user exceeds the threshold.

3. The system of claim 1, wherein the system is configured to send, using the cellular modem, the picture captured by the camera with the intoxication test result.

4. The system of claim 1, wherein the cellular modem is configured to report a movement of the vehicle.

5. The system of claim 1, wherein the cellular modem is configured to report an attempt to defeat the vehicle immobilization system.

6. The system of claim 1, wherein the system is configured to use the GPS receiver to detect if the vehicle is moving without a valid intoxication test result.

7. The system of claim 1, further comprising an accelerometer, wherein the system is configured to use the accelerometer to detect if the vehicle is moved without a valid intoxication test result.

8. The system of claim 1, wherein the cellular modem is configured to report information to a monitoring authority.

9. A method of selectively immobilizing a vehicle using a vehicle immobilization system based on a level of ethanol in a breath of a user, comprising:

detecting the level of ethanol in the breath of the user using a detection unit, the detection unit comprising:
a detection unit housing configured to be picked up and hand held by the user,
a fuel cell within the detection unit housing, wherein the fuel cell is operable to detect a presence of and a level of ethanol in a breath of the user,
a display operable to display text to the user,
a processor of the detection unit within the detection unit housing, the processor coupled to the display, and
a memory of the detection unit within the detection unit housing, the processor coupled to the processor of the detection unit, determining whether the level of ethanol in the breath of the user exceeds a threshold, sending, via a serial connection, a signal related to the level of ethanol in the breath of the user from the detection unit to a control module;

based on the signal related to the level of ethanol in the breath of the user from the detection unit, the control module selectively restricting operation of a vehicle by restricting operation of a starter of the vehicle based on the level of ethanol in the breath of the user exceeding the threshold, the control module comprising:

a processor of the control module operable to:
receive the signal related to the level of ethanol in the breath of the user from the detection unit,
based on the signal, selectively restrict the operation of the vehicle by restricting the operation of the starter of the vehicle based on the level of ethanol in the breath of the user exceeding the threshold; and
based on the signal, selectively allow the operation of the vehicle by allowing the operation of the starter of the vehicle based on the level of ethanol in the breath of the user not exceeding the threshold;

a memory of the control module connected to the processor of the control module and storing instructions for the processor of the control module to selectively restrict the operation of the vehicle by restricting the operation of the starter of the vehicle based on the level of ethanol in the breath of the user exceeding the threshold and selectively allow the operation of the vehicle by allowing the operation of the starter of the vehicle based on the level of ethanol in the breath of the user not exceeding the threshold;
wherein the control module is configured to be hidden under a dashboard in the vehicle and the detection unit is configured to be exposed for user interaction;
wherein the control module is physically separate from the detection unit housing and is connected to the detection unit via the serial connection;
sending an intoxication test result by a communication module physically separate from and external to the control module, the communication module comprising:
a global positioning system (GPS) receiver,
a cellular modem configured to send an intoxication test result associated with the level of ethanol in the breath of the user,
a processor of the communication module connected to the GPS receiver and the cellular modem, and
a memory of the communication module connected to the processor of the communication module,
wherein the communication module is coupled to the control module via a serial connector of the communication module;
wherein the GPS receiver and the cellular modem are coupled to a plurality of antennas integrated into the communication module; and
recording, via a camera, a picture of the user using the detection unit, wherein the camera is external to the control module, the communication module, and the detection unit, wherein the camera configured to connect to a USB interface, the camera comprising a cable connection to the vehicle immobilization system.

10. The method of claim 9, further comprising recording, using information from the GPS receiver, a location of the intoxication test.

11. The method of claim 9, further comprising reporting, using the cellular modem, attempts to defeat the system.

12. The method of claim 9, further comprising:
after allowing the operation of the vehicle by allowing the operation of the starter of the vehicle based on the level of ethanol in the breath of the user not exceeding the threshold, administer a re-test by prompting the user for a second breath of the user; and
based on the signal, selectively record a violation based on the level of ethanol in the breath of the user exceeding the threshold.

13. The method of claim 9, further comprising the control module recording a violation if the breath of the user exceeds the threshold.

14. The method of claim 9, further comprising sending, using the cellular modem, the picture captured by the camera with the intoxication test result.

15. The method of claim 9, further comprising reporting, using the cellular modem, a movement of the vehicle.

16. A method of installing a vehicle immobilization system in a vehicle, comprising:
installing a control module in a location hidden under a dashboard in a vehicle, wherein the control module is operable to selectively restrict operation of the vehicle by restricting operation of a starter of the vehicle, based on a level of ethanol in a breath of a user exceeding a threshold, the control module comprising:
a processor of the control module operable to:
receive a signal related to the level of ethanol in the breath of the user from the detection unit,
based on the signal, selectively restrict the operation of the vehicle by restricting the operation of the starter of the vehicle based on the level of ethanol in the breath of the user exceeding the threshold; and
based on the signal, selectively allow the operation of the vehicle by allowing the operation of the starter of the vehicle based on the level of ethanol in the breath of the user not exceeding the threshold;
a memory of the control module connected to the processor of the control module and storing instructions for the processor of the control module to selectively restrict the operation of the vehicle by restricting the operation of the starter of the vehicle based on the level of ethanol in the breath of the user exceeding the threshold and selectively allow the operation of the vehicle by allowing the operation of the starter of the vehicle based on the level of ethanol in the breath of the user not exceeding the threshold;
connecting the control module to a detection unit via a serial connection so that the detection unit is exposed for user interaction in the vehicle, wherein the detection unit comprises:
a detection unit housing physically separate from the control module, the detection unit housing configured to be picked up and hand held by the user,
a fuel cell within the detection unit housing and operable to detect a presence of and the level of ethanol in the breath of the user,
a display operable to display text to the user,
a processor of the detection unit coupled to the display,
a memory module of the detection unit coupled to the processor of the detection unit, and
wherein the detection unit is operable to send, to the control module and via the serial connection, the signal related to the level of ethanol in the breath of the user;
connecting a communication module to the control module via a serial connector of the communication module, wherein the communication module is physically separate from and external to the control module, the communication module comprising:
a global positioning system (GPS) receiver,
a cellular modem configured to send an intoxication test result associated with the level of ethanol in the breath of the user,
a processor of the communication module connected to the GPS receiver and the cellular modem, and
a memory of the communication module connected to the processor of the communication module,
wherein the GPS receiver and the cellular modem are coupled to a plurality of antennas integrated into the communication module; and
connecting a camera to the vehicle immobilization system using a cable connection, wherein the camera is external to the control module, the communication module, and the detection unit, wherein the camera is configured to connect to a USB interface, wherein the camera is configured to record a picture of the user using the detection unit.

17. The method of claim 16, wherein the control module is configured to record a violation if the breath of the user exceeds the threshold.

18. The method of claim 16, wherein the control module is configured to send, using the cellular modem, the picture captured by the camera with the intoxication test result.

19. The method of claim 16, wherein the cellular modem is configured to report a movement of the vehicle.

20. The method of claim 16, wherein the cellular modem is configured to report an attempt to defeat the vehicle immobilization system.

* * * * *